US011344121B2

(12) United States Patent
Choudhury

(10) Patent No.: US 11,344,121 B2
(45) Date of Patent: May 31, 2022

(54) METHODS OF PREDICTING PREECLAMPSIA USING BIOMARKERS

(71) Applicant: THE TEXAS A&M UNIVERSITY SYSTEM, College Station, TX (US)

(72) Inventor: Mahua Choudhury, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 212 days.

(21) Appl. No.: 16/092,820

(22) PCT Filed: Apr. 14, 2017

(86) PCT No.: PCT/US2017/027593
§ 371 (c)(1),
(2) Date: Oct. 11, 2018

(87) PCT Pub. No.: WO2017/180984
PCT Pub. Date: Oct. 19, 2017

(65) Prior Publication Data
US 2019/0055605 A1 Feb. 21, 2019

Related U.S. Application Data

(60) Provisional application No. 62/322,422, filed on Apr. 14, 2016.

(51) Int. Cl.
C12Q 1/68 (2018.01)
A47B 97/00 (2006.01)
A44B 11/00 (2006.01)
F16M 13/02 (2006.01)

(52) U.S. Cl.
CPC .............. *A47B 97/00* (2013.01); *A44B 11/00* (2013.01); *F16M 13/02* (2013.01); *A47B 2097/008* (2013.01)

(58) Field of Classification Search
None
See application file for complete search history.

(56) References Cited

U.S. PATENT DOCUMENTS

| 2007/0238124 | A1* | 10/2007 | Chibout | ............... | C12Q 1/6883 435/6.11 |
| 2010/0016173 | A1* | 1/2010 | Nagalla | ................ | G01N 33/689 506/9 |
| 2013/0245135 | A1 | 9/2013 | Winger et al. | | |
| 2013/0287772 | A1 | 10/2013 | Halbert et al. | | |
| 2014/0162888 | A1* | 6/2014 | Kuslich | ............ | G01N 33/57419 506/9 |
| 2015/0293115 | A1 | 10/2015 | Buhimschi et al. | | |
| 2016/0061824 | A1 | 3/2016 | Hahn et al. | | |

FOREIGN PATENT DOCUMENTS

| WO | WO 99/19502 | 4/1999 |
| WO | WO 03/016497 | 2/2003 |
| WO | WO 2014/143977 | 9/2014 |
| WO | WO 2015/002845 | 1/2015 |

OTHER PUBLICATIONS

"Pre-eclampsia", Wikipedia.com, accessed Sep. 26, 2020, pp. 1-10. (Year: 2020).*
Kumar, P. et al. "The c-Myc-Regulated MicroRNA-17~92 (miR-17~92) and miR-106a~363 Clusters Target hCYP19A1 and hGCM1 To Inhibit Human Trophoblast Differentiation" *Molecular and Cellular Biology*, May 2013, pp. 1782-1796, vol. 33, No. 9.
Wang, W. et al. "Preeclampsia Up-Regulates Angiogenesis-Associated MicroRNA (i.e., miR-17, -20a, and -20b) That Target Ephrin-B2 and EPHB4 in Human Placenta" *Journal of Clinical Endocrinology & Metabolism*, Jun. 2012, pp. E1051-E1059, vol. 97, No. 6.
Written Opinion in International Application No. PCT/US2017/027593, dated Jul. 26, 2017, pp. 1-11.
Hong, F. et al. "Decreased placental miR-I26 expression and vascular endothelial growth factor levels in patients with pre-eclampsia" *Journal of International Medical Research*, 2014, pp. 1243-1251, vol. 42, No. 6.
Wang, S. et al. "An Endothelial-specific microRNA Governs Vascular Integrity and Angiogenesis" *Developmental Cell*, Aug. 2008, pp. 1-25, vol. 15, No. 2.

* cited by examiner

*Primary Examiner* — Bradley L. Sisson
(74) *Attorney, Agent, or Firm* — Saliwanchik, Lloyd & Eisenschenk

(57) ABSTRACT

The subject invention pertains to biomarkers for identifying a subject as having high risk of the development PE. The biomarkers presented herein include miRNAs, post-translational modification of histone proteins, amount, expression and/or activity of histone or DNA modifying enzymes and methylation of sites in the genomic DNA. In certain embodiments, increased miR-17, increased acetylation of H4 histone protein, decreased amount, expression and/or activity of HDACS mRNA or protein or increased methylation of DNA at the genomic site CYP19A1 in the blood, serum or plasma of a subject compared to that of a control subject is used to predict the development of PE in the subject. The invention also provides kits and reagents to conduct assays to quantify biomarkers described herein. The invention further provides the methods of treating and/or managing PE in a subject identified as having a high risk of the development of PE.

7 Claims, 12 Drawing Sheets
(4 of 12 Drawing Sheet(s) Filed in Color)
Specification includes a Sequence Listing.

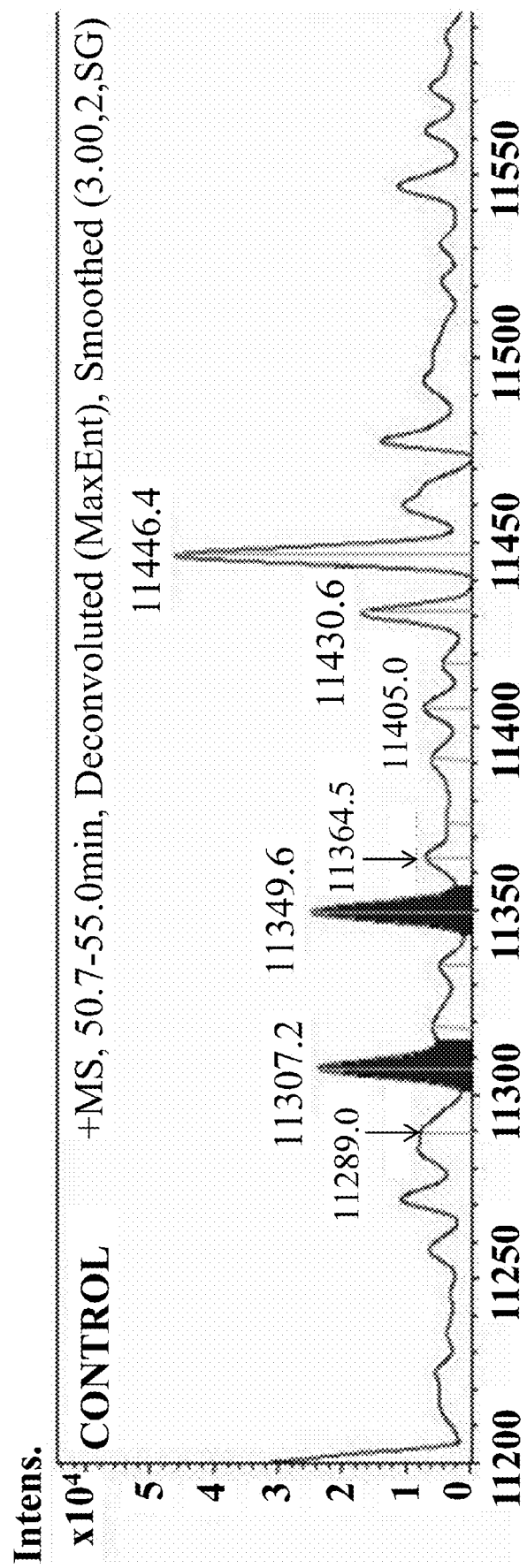
FIG. 2A(1)

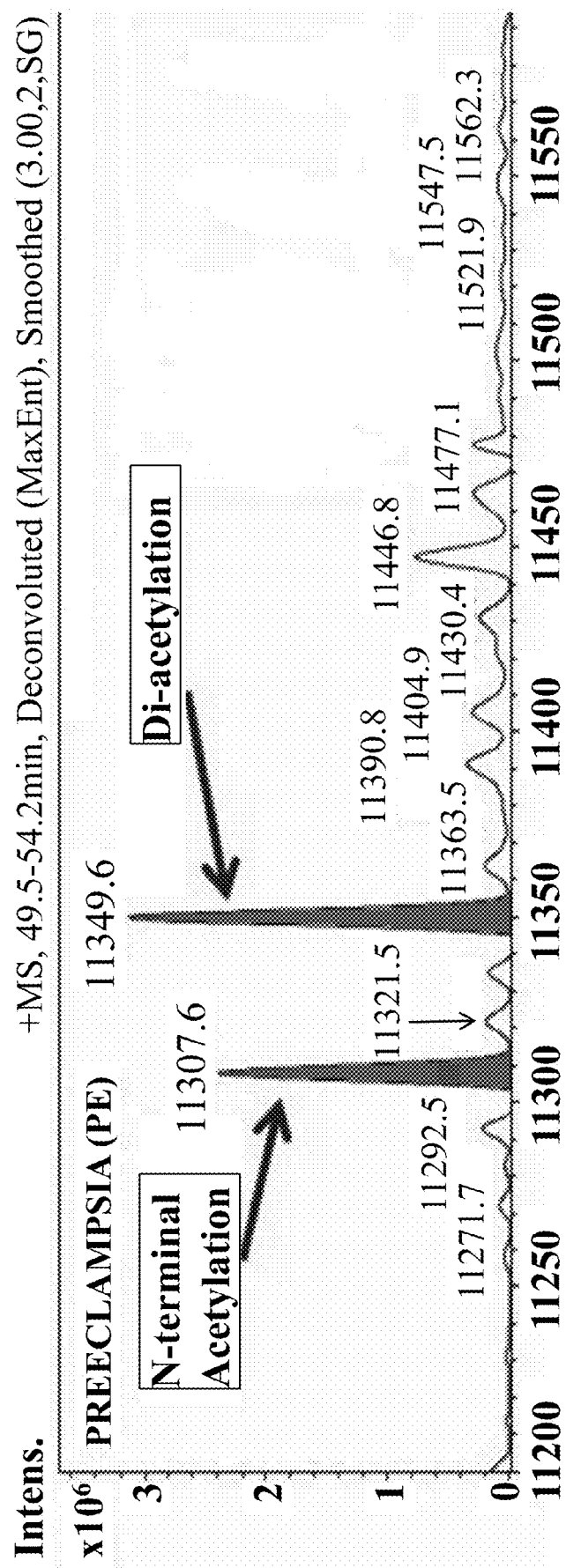
FIG. 2A(2)

METHODS OF PREDICTING PREECLAMPSIA USING BIOMARKERS

CROSS-REFERENCE TO RELATED APPLICATIONS

This application is the U.S. national stage application of International Patent Application No. PCT/US2017/027593, filed Apr. 14, 2017, which claims the benefit of U.S. Provisional Application Ser. No. 62/322,422, filed Apr. 14, 2016, the disclosures of which are hereby incorporated by reference in their entirety, including all figures, tables and amino acid or nucleic acid sequences.

The Sequence Listing for this application is labeled "Seq-List.txt" which was created on Apr. 14, 2017 and is 32 KB. The entire content of the sequence listing is incorporated herein by reference in its entirety.

BACKGROUND OF THE INVENTION

Preeclampsia (PE) is responsible for 76,000 maternal and 500,000 infant deaths worldwide each year. Adverse maternal events include stroke, organ dysfunction and disseminated intravascular coagulation; whereas, adverse fetal complications include intrauterine growth restriction, premature birth, and stillbirth. PE is also associated with increased risk of chronic diseases in the mother and child later in life. The cause of PE is unknown; however, it is often diagnosed in the third trimester and there is no known prevention or cure.

Most of the suggested biomarkers for PE focus on late gestation and lack sufficient sensitivity and specificity. Successful intervention of PE requires a better understanding of disease progression and development of accurate and early biomarkers that appear before the appearance of clinical symptoms. Placental DNA methylation and/or microRNA (miRNA) regulation, particularly, the presence of certain miRNAs in a mother's blood in the second or third trimester have been implicated in PE.

BRIEF SUMMARY OF THE INVENTION

The invention provides biomarkers which can be analyzed during the first trimester of pregnancy for identifying a subject as having high risk of the development PE later in the pregnancy. These noninvasive biomarkers presented herein include miRNAs, post-translational modification of histone proteins, amount, expression and/or activity of histone or DNA modifying enzymes and methylation of certain sites in the genomic DNA of certain cells in the mother.

Accordingly, in one embodiment, the levels of certain miRNAs in a body fluid, for example, blood, serum or plasma, of a subject are used to predict the development of PE. In another embodiment, the levels post-translational modifications of histone proteins in the cells, for example, blood cells, of a subject are used to predict the development of PE. In a further embodiment, the amounts, expression and/or activities of certain enzymes capable of modifying histone proteins or sites in the genomic DNA of cells, for example, blood cells, of a subject are used to predict the development of PE. In an even further embodiment, the levels of methylation of certain sites in the genomic DNA of cells, for example, blood cells, of a subject are used to predict the development of PE.

In an embodiment, increased miR-17 (SEQ ID NO: 77) in blood, serum or plasma of a subject compared to a control subject is used to predict the development of PE in the subject. In another embodiment, increased acetylation of H4 histone protein on N-terminus, lysine 12 and/or lysine 16 and/or methylation/demethylation on lysine 20 or a combination thereof compared to that of a control subject is used to predict the development of PE in the subject. In a further embodiment, decreased amount, expression and/or activity of HDAC5 protein or mRNA compared to that of a control subject is used to predict the development of PE in the subject. In an even further embodiment, hypermethylation of DNA at the genomic site CYP19A1 (SEQ ID NO: 46) compared to that of a control subject is used to predict the development of PE in the subject. In certain embodiment, increased mirR-17; increased acetylation of histone H4 on N-terminal, lysine 12 and/or lysine 16 and/or methylation/demethylation of lysine 20 or a combination thereof; decreased amount, expression and/or activity of HDAC5 protein or mRNA; and increased methylation of DNA in the genomic site CYP19A1 compared to that of a control sample are used to predict development of PE in the subject.

The invention also provides the methods of treating and/or managing PE in a subject identified as having a high risk of the development of PE.

The invention further provides kits and reagents to conduct assays to quantify biomarkers described herein.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 1A) Alterations in microRNA expression: The expression of 381 specific human microRNAs was profiled using TaqMan® Array Human MicroRNA Cards. The graph depicts the significant fold increase in 22 microRNAs after normalizing with U6 controls. All error bars, S.E.M.*p<0.03 were determined by one sample one-way t test; C=14, PE=14. FIG. 1B) Disease and functions associated with the significant upregulated microRNAs: Ingenuity Pathway Analysis (IPA) was carried out to identify significant disease and functions associated with the altered microRNAs (FIG. 1A). Threshold bar (black line) indicates cut-off point of significance p<0.05, using Fisher's exact test. Reproductive System Disease showed the most association with the significantly altered microRNAs. Other significant diseases and functions (e.g. inflammatory response, renal and urological disease, cardiovascular disease, cell death and survival) identified in the analysis are associated with PE pathogenesis. FIG. 1C) Screened microRNAs in the development of PE: 17 significant microRNAs (out of 22 significant microRNAs) are shown to be involved in the IPA gene database of pregnancy disorder, pregnancy induced hypertension, and PE (total 570 genes). The top three microRNAs (miR-296, miR-16-5p, and miR-17-5p) have the maximum number of targets. MiR-17 cluster (miR-17-5p and miR-19b) are shown (dark squares) to target highest number of genes (total 128). FIG. 1D) Expression of miR-17 and its cluster: Expression of mir-17 and its cluster miRNAs are shown. This selected group of miRNAs is involved in several pathways (angiogenesis, estrogen synthesis, invasion, etc.) which can lead to PE. miR-17 and its cluster show a consistent increase in all PE patients. All error bars, S.E.M*p<0.05 was determined by one sample one-way t test; C=14, PE=14.

FIGS. 2A-2B. Comparision of histone acetylation and histone deactylase profile in 1$^{st}$ trimester pregnant women who later developed PE and healthy pregnant women. Hyperacetylated histone H4: The post-translational modifications of histone H4 were characterized by LC-MS. The representative spectrum shows the acetylation profile of H4 for one control ((FIG. 2A(1))) and one PE case (FIG. 2A(2)) where mass 11307 Da corresponds to dimethylated monoacetylated histone H4 and mass 11349 Da corresponds to dimethylated diacetylated histone H4. The larger peak ratio (abundance of mass 11349/abundance of mass 11307) observed in the PE case corresponds to increased histone H4 diacetylation. FIG. 2B) Histone deacetylase gene expression: Customized qPCR Taqman plate was used to detect the expression levels of 81 epigenetic genes encoding enzymes known or predicted to modify genomic DNA and histones to regulate chromatin accessibility and gene expression. The graph depicts the alterations in 11 histone deacetylase genes in PE patients after normalizing with housekeeping gene 18S. All error bars, S.E.M.*$p<0.05$ determined by one sample one-way t test; C=10, PE=10.

BRIEF DESCRIPTION OF THE SEQUENCES

Figure 1A:
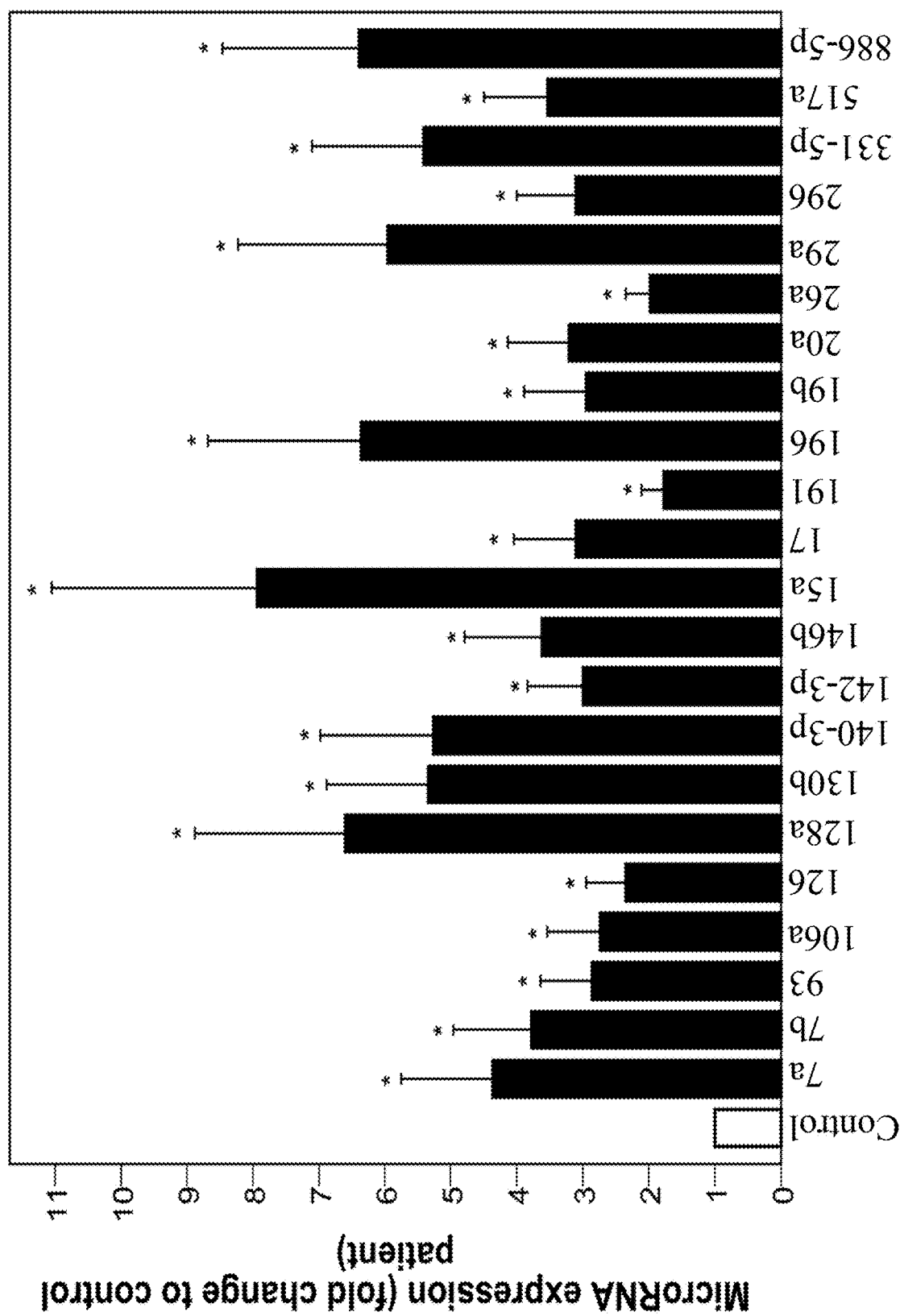
FIGS. 1A-1D. MicroRNA profile in 1$^{st}$ trimester pregnant women who later developed severe PE compared to healthy pregnant women.

SEQ ID NO: 1: Sequence of Histone H4 protein lacking the first methionine residue. The first methionine is removed from this sequence to correctly indicate the position for lysine residues, e.g., lysine 12, lysine 16 and lysine 20.

SEQ ID NOs: 2-45: Sequences of genomic DNA sites that are hypomethylated in PE patients.

SEQ ID NOs: 46-55: Sequences of genomic DNA sites that are hypermethylated in PE patients.

SEQ ID NOs: 56 to 115 and 191: Sequences of pre-miRNAs and mature miRNAs that are differentially expressed in PE patients.

| miRNA | SEQ ID NO: | Pre-miRNA | SEQ ID NO: | Mature miRNA |
|---|---|---|---|---|
| Hsa-miR-7c | 56 | GCAUCCGGGUUGAGGU AGUAGGUUGUAUGGU UUAGAGUUACACCCUG GGAGUUAACUGUACA ACCUUCUAGCUUUCCU UGGAGC | 57 | UGAGGUAGUAGG UUGUAUGGUU |
| Hsa-miR-93 | 58 | CUGGGGGCUCCAAAGU GCUGUUCGUGCAGGUA GUGUGAUUACCCAACC UACUGCUGAGCUAGCA CUUCCCGAGCCCCCGG | 59 | CAAAGUGCUGUU CGUGCAGGUAG |
| Hsa-miR-128a | 60 | UGAGCUGUUGGAUUC GGGGCCGUAGCACUGU CUGAGAGGUUUACAU UUCUCACAGUGAACCG GUCUCUUUUUCAGCUG CUUC | 61 | CGGGGCCGUAGC ACUGUCUGAGA |
| | | | OR | |
| | | | 191 | UCACAGUGAACC GGUCUCUUU |
| Hsa-miR-140-3p | 62 | UGUGUCUCUCUCUGUG UCCUGCCAGUGGUUUU ACCCUAUGGUAGGUUA CGUCAUGCUGUUCUAC CACAGGGUAGAACCAC GGACAGGAUACCGGGG CACC | 63 | UACCACAGGGUA GAACCACGG |
| Hsa-miR-142-3p | 64 | GACAGUGCAGUCACCC AUAAAGUAGAAAGCA CUACUAACAGCACUGG AGGGUGUAGUGUUUC CUACUUUAUGGAUGA GUGUACUGUG | 65 | UGUAGUGUUUCC UACUUUAUGGA |
| Hsa-miR-146b | 66 | CCUGGCACUGAGAACU GAAUUCCAUAGGCUGU GAGCUCUAGCAAUGCC CUGUGGACUCAGUUCU GGUGCCCGG | 67 | UGAGAACUGAAU UCCAUAGGCU |

-continued

| miRNA | SEQ ID NO: | Pre-miRNA | SEQ ID NO: | Mature miRNA |
|---|---|---|---|---|
| Hsa-miR-15a | 68 | CCUUGGAGUAAAGUA GCAGCACAUAAUGGUU UGUGGAUUUUGAAAA GGUGCAGGCCAUAUUG UGCUGCCUCAAAAAUA CAAGG | 69 | UAGCAGCACAUA AUGGUUUGUG |
| Hsa-miR-196b | 70 | ACUGGUCGGUGAUUU AGGUAGUUUCCUGUU GUUGGGAUCCACCUUU CUCUCGACAGCACGAC ACUGCCUUCAUUACUU CAGUUG | 71 | UAGGUAGUUUCC UGUUGUUGGG |
| Hsa-miR-331-5p | 72 | GAGUUUGGUUUUGUU UGGGUUUGUUCUAGG UAUGGUCCCAGGGAUC CCAGAUCAAACCAGGC CCCUGGGCCUAUCCUA GAACCAACCUAAGCUC | 73 | CUAGGUAUGGUC CCAGGGAUCC |
| Hsa-miR-886-5p | 74 | CACUCCUACCCGGGUC GGAGUUAGCUCAAGCG GUUACCUCCUCAUGCC GGACUUUCUAUCUGUC CAUCUCUGUGCUGGGG UUCGAGACCCGCGGGU GCUUACUGACCCUUUU AUGCAAUAA | 75 | CGGGUCGGAGUU AGCUCAAGCGG |
| Hsa-miR-17 | 76 | GUCAGAAUAAUGUCA AAGUGCUUACAGUGCA GGUAGUGAUAUGUGC AUCUACUGCAGUGAAG GCACUUGUAGCAUUAU GGUGAC | 77 | CAAAGUGCUUAC AGUGCAGGUAG |
| Hsa-miR-26a-5p | 78 | GUGGCCUCGUUCAAGU AAUCCAGGAUAGGCUG UGCAGGUCCCAAUGGG CCUAUUCUUGGUUACU UGCACGGGACGC | 79 | UUCAAGUAAUCC AGGAUAGGCU |
| Hsa-miR-26a-3p | 80 | GUGGCCUCGUUCAAGU AAUCCAGGAUAGGCUG UGCAGGUCCCAAUGGG CCUAUUCUUGGUUACU UGCACGGGACGC | 81 | CCUAUUCUUGGU UACUUGCACG |
| Hsa-miR-130b | 82 | GGCCUGCCCGACACUC UUUCCCUGUUGCACUA CUAUAGGCCGCUGGGA AGCAGUGCAAUGAUG AAAGGGCAUCGGUCAG GUC | 83 | ACUCUUUCCCUGU UGCACUAC |
| Hsa-miR-7a | 84 | AGGUUGAGGUAGUAG GUUGUAUAGUUUAGA AUUACAUCAAGGGAG AUAACUGUACAGCCUC CUAGCUUUCCU | 85 | UGAGGUAGUAGG UUGUAUAGUU |
| Hsa-miR-29a | 86 | AUGACUGAUUUCUUU UGGUGUUCAGAGUCA AUAUAAUUUUCUAGC ACCAUCUGAAAUCGGU UAU | 87 | ACUGAUUUCUUU UGGUGUUCAG |
| Hsa-miR-517a | 88 | UCUCAGGCAGUGACCC UCUAGAUGGAAGCACU GUCUGUUGUAUAAAA GAAAAGAUCGUGCAUC CCUUUAGAGUGUUACU GUUUGAGA | 89 | CCUCUAGAUGGA AGCACUGUCU |

-continued

| miRNA | SEQ ID NO: | Pre-miRNA | SEQ ID NO: | Mature miRNA |
|---|---|---|---|---|
| Hsa-miR-191 | 90 | CGGCUGGACAGCGGGC AACGGAAUCCCAAAAG CAGCUGUUGUCUCCAG AGCAUUCCAGCUGCGC UUGGAUUUCGUCCCCU GCUCUCCUGCCU | 91 | CAACGGAAUCCCA AAAGCAGCUG |
| Hsa-miR-296 | 92 | AGGACCCUUCCAGAGG GCCCCCCCUCAAUCCU GUUGUGCCUAAUUCAG AGGGUUGGGUGGAGG CUCUCCUGAAGGGCUC U | 93 | AGGGCCCCCCCUC AAUCCUGU |
| Hsa-miR-18a | 94 | UGUUCUAAGGUGCAUC UAGUGCAGAUAGUGA AGUAGAUUAGCAUCU ACUGCCCUAAGUGCUC CUUCUGGCA | 95 | UAAGGUGCAUCU AGUGCAGAUAG |
| Hsa-miR-19a | 96 | GCAGUCCUCUGUUAGU UUUGCAUAGUUGCACU ACAAGAAGAAUGUAG UUGUGCAAAUCUAUGC AAAACUGAUGGUGGCC UGC | 97 | AGUUUUGCAUAG UUGCACUACA |
| Hsa-miR-20a | 98 | GUAGCACUAAAGUGCU UAUAGUGCAGGUAGU GUUUAGUUAUCUACU GCAUUAUGAGCACUUA AAGUACUGC | 99 | UAAAGUGCUUAU AGUGCAGGUAG |
| Hsa-miR-19b-1 | 100 | CACUGUUCUAUGGUUA GUUUUGCAGGUUUGC AUCCAGCUGUGUGAUA UUCUGCUGUGCAAAUC CAUGCAAAACUGACUG UGGUAGUG | 101 | AGUUUUGCAGGU UUGCAUCCAGC |
| Hsa-miR-92a-1 | 102 | CUUUCUACACAGGUUG GGAUCGGUUGCAAUGC UGUGUUUCUGUAUGG UAUUGCACUUGUCCCG GCCUGUUGAGUUUGG | 103 | AGGUUGGGAUCG GUUGCAAUGCU |
| Hsa-miR-106a | 104 | CCUUGGCCAUGUAAAA GUGCUUACAGUGCAGG UAGCUUUUUGAGAUC UACUGCAAUGUAAGCA CUUCUUACAUUACCAU GG | 105 | AAAAGUGCUUAC AGUGCAGGUAG |
| Hsa-miR-18b | 106 | UGUGUUAAGGUGCAU CUAGUGCAGUUAGUG AAGCAGCUUAGAAUCU ACUGCCCUAAAUGCCC CUUCUGGCA | 107 | UAAGGUGCAUCU AGUGCAGUUAG |
| Hsa-miR-20b | 108 | AGUACCAAAGUGCUCA UAGUGCAGGUAGUUU UGGCAUGACUCUACUG UAGUAUGGGCACUUCC AGUACU | 109 | CAAAGUGCUCAU AGUGCAGGUAG |
| Hsa-miR-19b-2 | 110 | ACAUUGCUACUUACAA UUAGUUUUGCAGGUU UGCAUUUCAGCGUAUA UAUGUAUAUGUGGCU GUGCAAAUCCAUGCAA AACUGAUUGUGAUAA UGU | 111 | AGUUUUGCAGGU UUGCAUUUCA |

-continued

| miRNA | SEQ ID NO: | Pre-miRNA | SEQ ID NO: | Mature miRNA |
|---|---|---|---|---|
| Hsa-miR-92a-2 | 112 | UCAUCCCUGGGUGGGG AUUUGUUGCAUUACU UGUGUUCUAUAUAAA GUAUUGCACUUGUCCC GGCCUGUGGAAGA | 113 | GGGUGGGGAUUU GUUGCAUUAC |
| Hsa-miR-363 | 114 | UGUUGUCGGGUGGAU CACGAUGCAAUUUUGA UGAGUAUCAUAGGAG AAAAAUUGCACGGUA UCCAUCUGUAAACC | 115 | CGGGUGGAUCAC GAUGCAAUUU |

SEQ ID NOs: 116-190: Sequences of the probes for determining methylation of the genomic sites that are differentially methylated in PE patients.

DETAILED DISCLOSURE OF THE INVENTION

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

"Treatment", "treating", "palliating" and "ameliorating" (and grammatical variants of these terms), as used herein, are used interchangeably. These terms refer to an approach for obtaining beneficial or desired results including but not limited to therapeutic benefit. A therapeutic benefit is achieved with the eradication or amelioration of one or more of the physiological symptoms associated with PE such that an improvement is observed in the patient, notwithstanding that the patient may still be afflicted with PE.

"Subject" refers to an animal, such as a mammal, for example a human. The methods described herein can be useful in both humans and non-human animals. In some embodiments, the subject is a mammal (such as an animal model of disease), and in some embodiments, the subject is human. The terms "subject" and "patient" can be used interchangeably.

Epigenetic dysregulation during early pregnancy may lead to PE. DNA methylation, histone modification, and miRNA are all inter-related and may work in concert to regulate gene expression leading to PE. The current invention provides that alterations in epigenetic features and miRNA could presage PE and be reflected in tissues of the pregnant mother, for example, during the first trimester in the blood of a pregnant mother who later developed PE.

To discover early noninvasive novel biomarkers of PE, epigenetic (DNA methylation, histone modification, and epigenetic modifying enzyme) and miRNA profiling was conducted in a case-controlled study in the first trimester in tissues of pregnant mothers, for example, in blood of pregnant mothers. Altered expressions of certain miRNA (e.g., upregulated miR-17); altered post-translational modifications of certain histone proteins (e.g., hyperacetylation of H4); altered expression, amount and/or activity of certain histone or DNA modifying enzymes (e.g., decreased HDAC5 protein and/or mRNA); and/or altered methylation of certain genomic DNA sites (e.g., hypermethylated CYP19A1) were found to be interrelated and associated with the development of PE.

Accordingly, an embodiment of the invention provides a method of predicting the development of PE in a subject, the method comprising:

(a) determining the level of one or more miRNAs in:
  i) a test sample obtained from the subject, and
  ii) optionally a control sample;

(b) optionally obtaining one or more reference values corresponding to levels of one or miRNAs,
  wherein the presence of the one or more miRNAs:
  at different levels in the test sample as compared to the control sample, or relative to the reference values indicates high risk of development of PE in the subject; and (c) identifying the subject as having high risk of developing PE based on the level of one or more miRNAs in the test sample and optionally, administering a therapy to the subject to treat and/or manage PE, or (d) identifying the subject as not having high risk of developing PE based on the level of one or more miRNAs in the test sample and withholding the therapy to the subject to treat and/or manage PE.

Various techniques are well known to a person of ordinary skill in the art to determine the level of miRNA in a sample. Non-limiting examples of such techniques include microarray analysis, real-time polymerase chain reaction (PCR), Northern blot, in situ hybridization, solution hybridization, or quantitative reverse transcription PCR (qRT-PCR). Methods of carrying out these techniques are routine in the art. Additional methods of determining the level of miRNA in a sample are also well known to a person of ordinary skill in the art and such embodiments are within the purview of the invention.

The reference values corresponding to levels of one or miRNAs indicate the level of miRNA associated with no risk or low risk of the development of PE or high risk of development of PE. As such, the reference values corresponding to levels of one or miRNAs may be indicative of the absence or presence of high risk of the development of PE. A reference value associated with no risk or low risk of the development of PE may be obtained based on samples obtained from subjects known to be free of PE. A reference value associated with high risk of the development of PE may be obtained based on samples obtained from subjects known to have PE.

For example, tissues from a group of pregnant women can obtained during the first trimester and the levels of one or more miRNAs can be determined. The group of women can then be monitored for the development of PE. Reference values corresponding to levels of one or more miRNAs that are associated with low risk or no risk of the development of PE or high risk of the development of PE can be determined based on the presence of absence of PE in various women whose samples were analyzed. Additional examples of determining references values associated with no risk or low risk or high risk of the development of PE are well known to a person of ordinary skill in the art and such embodiments are within the purview of the invention.

The step of identifying the subject as having high risk or not having high risk of developing PE depends on the level of one or more miRNAs in the test sample. For example, if the levels of certain miRNAs in the test sample are significant higher or lower than the levels of corresponding miRNAs in the control sample, the subject is identified as having high risk of development of PE. For example, if the levels of one or more of miR-7a, miR-7c, miR-93, mir-106a, mir-126, miR-128a, miR-130b, miR-140-3p, miR-142-3p, miR-146b, miR-15a-5p, miR-17, miR-191, miR-196, miR-19b-1, miR-20a, miR-331-5p, miR-886-5p, miR-26a, miR-29a, miR-517a and miR-296 miRNAs are higher in the test sample compared to control sample, the subject is identified as having high risk of the development of PE (See Table 1). Thus, a woman is identified as having high risk of the development of PE if the levels of one or more of miR-7a, miR-7c, miR-93, mir-106a, mir-126, miR-128a, miR-130b, miR-140-3p, miR-142-3p, miR-146b, miR-15a-5p, miR-17, miR-191, miR-196, miR-19b-1, miR-20a, miR-331-5p, miR-886-5p, miR-26a, miR-29a, miR-517a and miR-296, are higher in a blood, serum or plasma sample of the woman compared to a control sample.

A further embodiment of the invention provides a kit comprising reagents to carry out the methods of the current invention. In one embodiment, the kit comprises primers or probes specific for miRNAs of interest. Reagents for treating the samples, for example, deproteination, degradation of DNA, or removal of other impurities can also be provided in the kit.

An aspect of the invention provides a kit, for example, a point-of-care (POC) diagnostic device for assaying one or more miRNAs which can be used to identify the subject as having high risk of the development PE. In another embodiment, the kit comprises an oligonucleotide chip and reagents to conduct the assay to determine the levels of miRNAs corresponding to the oligonucleotides on the oligonucleotide chip. The oligonucleotide chip according to the invention contains oligonucleotides corresponding to a group of miRNAs that are present at different levels in a sample of an individual having a high risk of the development of PE as compared to the corresponding sample of an individual having no risk or low risk of the development of PE.

In one embodiment, the oligonucleotide chip essentially consists of oligonucleotides corresponding to one or more miRNAs selected from miR-7c, miR-93, miR-128a, miR-140-3p, miR-142-3p, miR-146b, miR-15a, miR-196b, miR-331-5p, miR-886-5p, miR-17, miR-26a, miR-130b, miR-7a, miR-29a, miR-517a, miR-191, miR-296, miR-18a, miR-19a, miR-20a, miR-19b-1, miR-92a-1, miR-106a, miR-18b, miR-20b, miR-19b-2, miR-92a-2, and miR-363 and optionally, one or more control oligonucleotides.

For the purposes of the invention, the term "oligonucleotide chip essentially consists of oligonucleotides" indicates that the oligonucleotide chip contains oligonucleotides corresponding to only those miRNAs that present at different levels in a sample of an individual having a high risk of the development of PE as compared to the corresponding

TABLE 1 miRNA significantly higher in a PE sample compared to a control sample.

| mi-RNA | Mean | Std. Error of Mean | Median | Minimum | Maximum | Std. Deviation | p-value |
|---|---|---|---|---|---|---|---|
| mir7a | 4.3634 | 1.3870 | 2.3007 | 0.0243 | 16.2470 | 5.1897 | 0.015 |
| mir7c | 3.7766 | 1.1799 | 1.6092 | 0.1085 | 12.4587 | 4.4148 | 0.018 |
| mir93 | 2.8628 | 0.7776 | 2.3524 | 0.0349 | 9.6843 | 2.9093 | 0.016 |
| mir106a | 2.7417 | 0.7952 | 1.2418 | 0.0599 | 8.7076 | 2.9752 | 0.024 |
| mir126 | 2.3437 | 0.6060 | 1.1842 | 0.0555 | 6.5371 | 2.2675 | 0.023 |
| mir128a | 6.6042 | 2.2748 | 3.6634 | 0.0162 | 30.0607 | 8.5116 | 0.014 |
| mir130b | 5.3420 | 1.5437 | 3.3804 | 0.0066 | 18.8090 | 5.7760 | 0.007 |
| mir140-3p | 5.2632 | 1.7166 | 2.9218 | 0.0858 | 20.6024 | 6.4230 | 0.014 |
| mir142-3p | 2.9965 | 0.8411 | 1.5552 | 0.0206 | 9.9850 | 3.1473 | 0.017 |
| mir146b | 3.6190 | 1.1652 | 0.9302 | 0.0472 | 12.3514 | 4.3598 | 0.021 |
| mir15a | 7.9395 | 3.1094 | 0.8989 | 0.0922 | 35.0204 | 11.6341 | 0.022 |
| mir17 | 3.1044 | 0.9355 | 1.5041 | 0.0580 | 10.9931 | 3.5002 | 0.021 |
| mir191 | 1.7720 | 0.3352 | 1.7303 | 0.0669 | 4.1845 | 1.2541 | 0.019 |
| mir196b | 6.3686 | 2.3113 | 2.5740 | 0.0979 | 28.4629 | 8.6479 | 0.019 |
| mir19b | 2.9521 | 0.9334 | 1.3627 | 0.0319 | 11.1013 | 3.4926 | 0.028 |
| mir20a | 3.2121 | 0.9201 | 1.2467 | 0.0328 | 10.1598 | 3.4427 | 0.016 |
| mir26a | 1.9812 | 0.3617 | 1.8041 | 0.0173 | 4.3605 | 1.3534 | 0.009 |
| mir29a | 5.9577 | 2.2675 | 2.2709 | 0.1725 | 28.0031 | 8.4840 | 0.024 |
| mir296 | 3.1084 | 0.8898 | 1.7807 | 0.0478 | 9.6324 | 3.3293 | 0.017 |
| mir331-5p | 5.4130 | 1.6932 | 1.4936 | 0.0979 | 16.1418 | 6.3354 | 0.011 |
| mir517a | 3.5323 | 0.9610 | 2.2434 | 0.0048 | 10.2401 | 3.5957 | 0.01 |
| mir886-5p | 6.3978 | 2.0627 | 3.1252 | 0.0753 | 21.2943 | 7.7179 | 0.011 | sample of an individual having no risk or low risk of the development of PE and optionally, contain one or more control oligonucleotides.

The control oligonucleotides are oligonucleotides corresponding to an miRNA or messenger RNAs (mRNA) known to be present in the equal amount in a sample of an individual having a high risk of the development of PE as compared to the corresponding sample of an individual having no risk or low risk of the development of PE. Non-limiting examples of control oligonucleotides include oligonucleotides corresponding to mRNAs of 18S, U6 form microRNA, β-actin, β-glucoronidase and Glyceraldehyde-3-phosphate dehydrogenase (GAPDH). Additional examples of control miRNAs or mRNAs depend on the tissue under examination. A person of ordinary skill in the art can determine control oligonucleotides appropriate for a particular assay and such embodiments are within the purview of the invention.

Epigenetic biomarkers of PE according to the invention include post-translational modification of one or more histone proteins. Accordingly, an embodiment of the invention also provides a method of predicting the development PE in a subject, the method comprising:

(a) determining the levels of post-translational modifications of one or more histone proteins in:

i) a test sample obtained from the subject, and ii) optionally a control sample;

(b) optionally obtaining one or more reference values corresponding to the levels of post-translational modifications of the one or more histone proteins, wherein the presence of the post-translational modifications in the one or more histone proteins:

at different levels in the test sample as compared to the control sample, or relative to the reference values indicates high risk of development of PE in the subject; and (c) identifying the subject as having high risk of developing PE based the levels of post-translational modifications in the one or more histone proteins in the test sample and optionally, administering a therapy to the subject to treat and/or manage PE, or (d) identifying the subject as having not having high risk of developing PE based on the levels of post-translational modifications in the one or more histone proteins in the test sample and withholding the therapy to the subject to treat and/or manage PE.

Non-limiting examples of post-translational modifications of histone proteins include methylation, acetylation, ADP-ribosylation, ubiquitination, citrullination, and phosphorylation. The one or more histones can be selected from H1, H2A, H2B, H3, H4 and H5. In one embodiment, hyperacetylation of H3 is indicative of the development of PE.

Various techniques are well known to a person of ordinary skill in the art to determine the level of post-translational modifications of one or more histone proteins in a sample. Non-limiting examples of such techniques include protein mass-spectrometry and antibody based analysis.

Determination of post-translation modification of a histone protein by protein spectrometry in a sample involves analyzing protein lysates or purified histone protein from a sample and analyze them by mass spectrometry to identify specific peptides within the histone protein which have different spectrometric behavior based on the presence or absence of post-translational modifications, for example, acetylation, methylation, demethylation. Certain techniques of spectrometric analysis of post-translational modification of proteins are described in Harvey (2005), which is herein incorporated by reference in its entirety.

In a further embodiment, post-translational modification of a histone protein is determined in an antibody based assay using antibody specific for a post-translational modification. For example, acetylation of H4 histone protein on one or more of: N-terminus, Lysine 12, Lysine 16 and methylation/dimethylation on Lysine 20 is determined in an antibody based assay using antibody specific for the recited modification. In another embodiment, two or more antibodies specific for different post-translational modification are used to determine post-translational modification of a histone protein. Non-limiting examples of the antibody based assays include western blot analysis, enzyme immunoassay (EIA), enzyme linked immunosorbent assay (ELISA), radioimmune assay (MA) and antigen-antibody precipitation assay. Additional examples of antibody-based assays are well known to a person of ordinary skill in the art and such embodiments are within the purview of the current invention.

Methods of carrying out these techniques are routine in the art. Additional methods of determining the level post-translational modifications of histone proteins in a sample are also well known to a person of ordinary skill in the art and such embodiments are within the purview of the invention.

The reference value corresponding to levels of post-translational modifications of one or more histone proteins indicate the level of post-translational modifications associated with no risk or low risk of the development of PE or high risk of development of PE. As such, the reference values corresponding to levels of post-translational modifications of certain histone proteins may be indicative of the absence or presence of high risk of the development of PE. A reference value associated with no risk or low risk of the development of PE may be obtained based on samples obtained from subjects known to be free of PE. A reference value associated with high risk of the development of PE may be obtained based on samples obtained from subjects known to have PE. For example, tissues from a group of pregnant women can obtained during the first trimester and the levels of post-translational modifications of one or more histone proteins can be determined. The group of women can then be monitored for the development of PE. Reference values corresponding to levels of post-translational modifications of one or more histone proteins that are associated with low risk or no risk of the development of PE or high risk of the development of PE can be determined based on the presence of absence of PE in various women whose samples were analyzed. Additional examples of determining references values associated with no risk or low risk or high risk of the development of PE are well known to a person of ordinary skill in the art and such embodiments are within the purview of the invention.

The step of identifying the subject as having high risk or not having high risk of developing PE depends on the level of post-translational modifications of one or more histone proteins in the test sample. For example, if the levels of certain post-translational modifications of certain histone proteins in the test sample are significant higher or lower than the levels of corresponding post-translational modifications of certain histone proteins in the control sample, the subject is identified as having high risk of development of PE.

For example, a subject is identified as having high risk of the development of PE if H4 histone in a sample from the subject has one or more of:

a) increased acetylation on N-terminus,
b) increased acetylation on Lysine 12,
c) increased acetylation on lysine 16, and
d) increased methylation/demethylation on lysine 20.

In another example, a woman is identified as having high risk of the development of PE if H4 histone protein (SGRGKGGKGLGKGGAKRHRKVLRD-NIQGITKPAIRRL ARRGGVKRISGLIY-EETRGVLKVFLENVIRDAVTYTEHAKRKTVTAMDV-VYALKRQ GRTLYGFGG, SEQ ID NO: 1) in a buffy coat sample of blood from the woman has one or more of:
a) increased acetylation on N-terminus,
b) increased acetylation on Lysine 12,
c) increased acetylation on lysine 16, and/or
d) increased methylation/demethylation on lysine 20.

A further embodiment of the invention provides a kit comprising reagents to carry out the methods of the current invention, for example, identifying a subject as having high risk of the development of PE and optionally, administering therapy to treat and/or manage PE in the subject. The kit comprises reagents to conduct the assay to determine the levels of certain post-translational modifications of certain histones, for example, an antibody chip containing specific antibodies.

An aspect of the invention provides a kit, for example, POC diagnostic device for assaying one or more post-translational modifications of histone proteins which can be used to identify the subject as having high risk of the development PE. The antibody chip according to the invention comprises or essentially consists of antibodies against histone proteins post-translationally modified on certain residues, wherein the histone proteins are post-translationally modified on certain residues at different levels in a sample of an individual having a high risk of the development of PE as compared to the corresponding sample of an individual having no risk or low risk of the development of PE.

In one embodiment, the antibody chip essentially consists of one or more of antibodies against:
a) human H4 histone protein acetylated on N-terminus,
b) human H4 histone protein acetylation on Lysine 12,
c) human H4 histone protein acetylation on lysine 16, and
d) human H4 histone protein methylation/demethylation on lysine 20.

For the purposes of the invention, the term "antibody chip essentially consists of antibodies" indicates that the antibody chip contains antibodies against only those post-translationally modified histone proteins that are modified at different levels in a sample of an individual having a high risk of the development of PE as compared to the corresponding sample of an individual having no risk or low risk of the development of PE and optionally, contain one or more control antibodies. The control antibodies can bind to histone proteins regardless of the post-translational modification. Thus, control antibodies can be used to determine the level of certain histone proteins; whereas, the post-translational modification specific antibodies can be used to determine the level of certain post-translational modifications in those histone proteins.

Epigenetic biomarkers of PE according to the invention also include expression, amount and/or activity of histone and DNA modifying enzymes, i.e., one or more enzymes that mediate post-translational modification of histone proteins or modification of DNA, for example, methylation. Accordingly, an embodiment of the invention also provides a method of predicting the development of PE in a subject, the method comprising:

(a) determining the levels of expression, activity and/or amount of one or more histone or DNA modifying enzymes in:
i) a test sample obtained from the subject, and
ii) optionally a control sample;

(b) optionally obtaining one or more reference values corresponding to the levels of expression, activity and/or amount histone proteins or DNA modifying enzymes, wherein the presence of expression, activity and/or amount of one or more histone or DNA modifying enzymes:
at different levels in the test sample as compared to the control sample, or
relative to the reference values indicates high risk of development of PE in the subject; and (c) identifying the subject as having high risk of developing PE based on the levels of one or more histone or DNA modifying enzymes in the test sample and optionally, administering a therapy to the subject to treat and/or manage PE, or (d) identifying the subject as not having high risk of developing PE based on the levels of one or more histone or DNA modifying enzymes in the test sample and withholding the therapy to the subject to treat and/or manage PE if the subject.

Non-limiting examples of modifications of histone proteins include methylation, acetylation, ADP-ribosylation, ubiquitination, citrullination, and phosphorylation. Non-limiting examples of histone modifying enzymes include histone acetyl transferase (HAT), histone deacetylase (HDAC), histone methyltransferase (HMT) and histone demethylase. Non-limiting examples of DNA modifying enzymes include DNA methyl transferase (DNMT). Additional examples of enzymes involved in modifying histone proteins or DNA are well known to a person of ordinary skill in the art and such embodiments are within the purview of the invention.

The activity of histone or DNA modifying enzymes in the test sample and optionally, the control sample can be determined by assays to determine the activity of histone or DNA modifying activity, expression and/or amount of histone or DNA modifying enzyme, expression and/or amount of mRNA encoding histone or DNA modifying enzyme. Various techniques are well known to a person of ordinary skill in the art to determine the level of expression, amount and/or activity of one or more histone or DNA modifying enzymes or the corresponding mRNAs. Non-limiting examples of techniques used to determine the activity histone or DNA modifying enzymes include fluorometric and colorimetric assays; whereas, techniques used to determine histone or DNA modifying enzyme amount include mass spectrometry or antibody based assays. Example of techniques used to determine activity of histone or DNA modifying enzymes are well known to a person of ordinary skill in the art and such methods are within the purview of the invention.

Determination of the amount of an enzyme by protein spectrometry in a sample involves analyzing protein lysates or purified enzymes of interest from a sample by mass spectrometry to identify the amounts of specific peptides within the histone protein. The amounts of enzymes within a sample can be determined based on the amount of peptides originating from the enzyme in the sample.

Non-limiting examples of the antibody based assays which can be used to determine the amount of histone or DNA modifying enzymes in a sample include western blot analysis, EIA, ELISA, RIA and antigen-antibody precipitation assay. Additional examples of antibody-based assays are well known to a person of ordinary skill in the art and such embodiments are within the purview of the current invention.

Methods of carrying out these techniques are routine in the art. Additional methods of determining the level amount or activity of histone or DNA modifying enzymes in a sample are also well known to a person of ordinary skill in the art and such embodiments are within the purview of the invention.

The reference value corresponding to levels of expression, amount and/or activity of histone or DNA modifying enzymes indicate the levels associated with no risk or low risk of the development of PE or high risk of development of PE. As such, the reference values corresponding to levels of expression, amount and/or activity of histone or DNA modifying enzymes may be indicative of the absence or presence of high risk of the development of PE. A reference value associated with no risk or low risk of the development of PE may be obtained based on samples obtained from subjects known to be free of PE. A reference value associated with high risk of the development of PE may be obtained based on samples obtained from subjects known to have PE. For example, tissues from a group of pregnant women can obtained during the first trimester and the levels of expression, amount and/or activity of histone or DNA modifying enzymes can be determined. The group of women can then be monitored for the development of PE. Reference values corresponding to levels of expression, amount and/or activity of histone or DNA modifying enzymes that are associated with low risk or no risk of the development of PE or high risk of the development of PE can be determined based on the presence of absence of PE in various women whose samples were analyzed. Additional examples of determining references values associated with no risk or low risk or high risk of the development of PE are well known to a person of ordinary skill in the art and such embodiments are within the purview of the invention.

The step of identifying the subject as having high risk or not having high risk of developing PE depends on the level of expression, amount and/or activity of histone or DNA modifying enzymes in the test sample. For example, if the levels of expression, amount and/or activity certain of histone or DNA modifying enzymes in the test sample are significant higher or lower than the levels of corresponding enzymes in the control sample, the subject is identified as having high risk of development of PE.

In one embodiment, a subject is identified as having high risk of the development of PE if histone deacetylase 1 (HDAC1) protein, mRNA or activity is increased in a test sample as compared to a control sample or histone deacetylase 5 (HDAC5) protein, mRNA or activity is decreased in a test sample as compared to a control sample. In another example, a woman is identified as having high risk of the development of PE if the HDAC1 protein, mRNA or activity is increased in a buffy coat sample of blood from the woman as compared to a control sample or HDAC5 protein, mRNA or activity is decreased in a buffy coat sample of blood from the woman as compared to a control sample.

Figure 5:
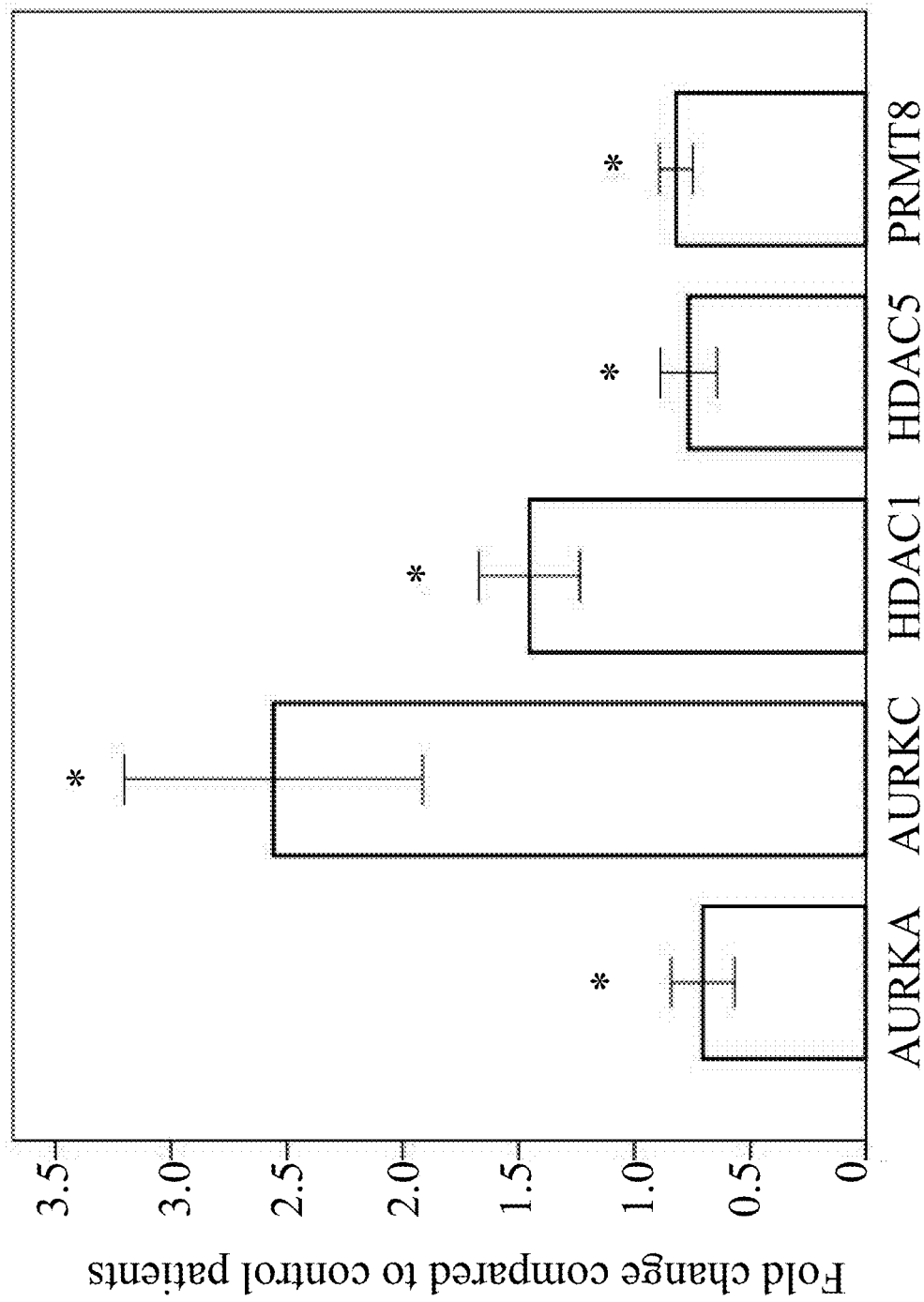
FIG. 5. Upregulated or downregulated histones or DNA modifying enzymes in PE patients. $p=0.03$ for all; $p=0.04$ for hdac5.
Figure 6:
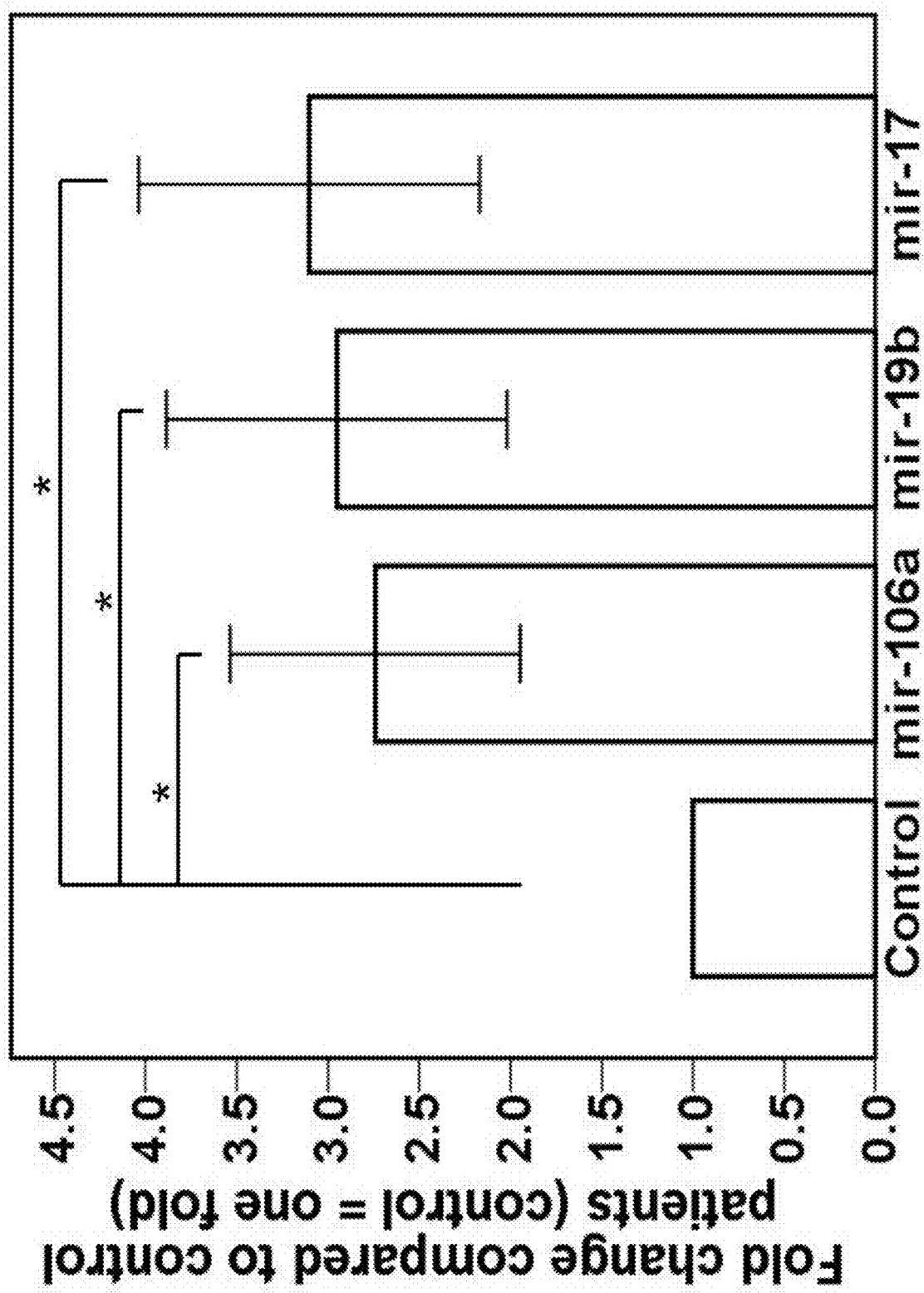
FIG. 6 and FIG. 7. Upregulated miRNAs and specific combinations of mRNAs upregulated in PE patients.
Figure 7:
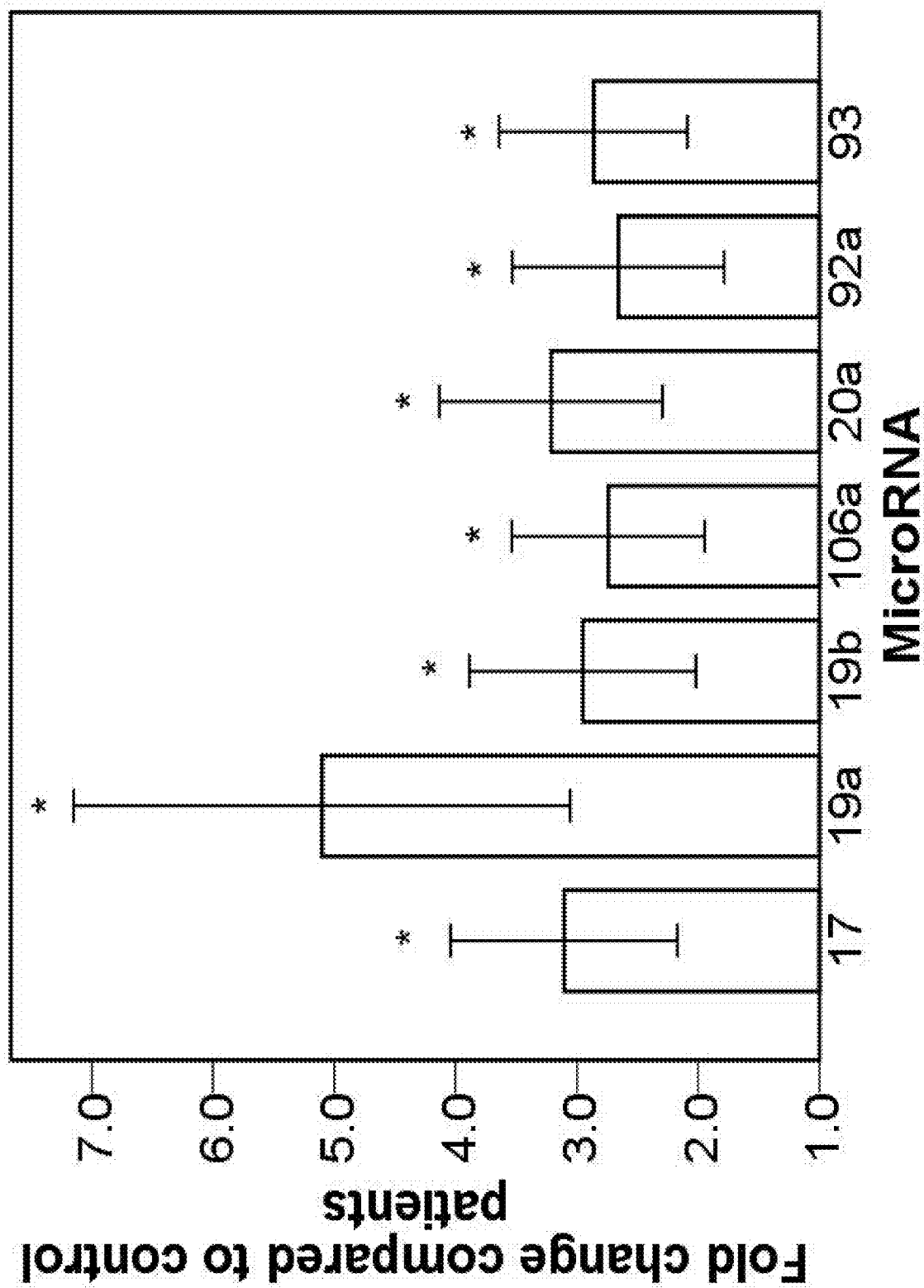

Alternately, if the level of Aurora Kinase C (AURKC) protein, mRNA or activity is higher in the test sample compared to the control sample, the subject is identified as having high risk of developing PE (FIG. 5).

Further, if the level of Aurora Kinase A (AURKA) or protein arginine N-methyltransferase 8 (PRMT8) protein, mRNA or activity is lower in the test sample compared to the control sample, the subject is identified as having high risk of developing PE (FIG. 5).

A further embodiment of the invention provides a kit comprising reagents to carry out the methods of the current invention, for example, identifying a subject as having high risk of the development of PE and optionally, administering therapy to treat and/or manage PE in the subject. The kit comprises reagents to conduct the assay to determine the levels of expression, amount and/or activity of certain histone or DNA modifying enzymes, for example, an antibody chip containing antibodies against certain histone or DNA modifying enzymes or oligonucleotide chips containing mRNAs corresponding to certain histone or DNA modifying enzymes.

The antibody chip or oligonucleotide chip according to the invention contains antibodies or oligonucleotides corresponding to certain histone or DNA modifying enzymes, wherein the histone or DNA modifying enzymes have different amount, expression and/or activity in a sample of an individual having a high risk of the development of PE as compared to the corresponding sample of an individual having no risk or low risk of the development of PE and optionally, contain one or more control antibodies or control oligonucleotides.

In one embodiment, the antibody chip essentially consists of an antibody against HDAC1 and an antibody against HDAC5; whereas, the oligonucleotide chip essentially consists of an oligonucleotide corresponding to HDAC1 mRNA and an oligonucleotide corresponding to HDAC5 mRNA.

For the purposes of the invention, the term "chip essentially consists of antibodies or oligonucleotides" indicates that the antibody or oligonucleotide chip contains antibodies or oligonucleotides corresponding only those histone or DNA modifying enzymes that are present at different levels in a sample of an individual having a high risk of the development of PE as compared to the corresponding sample of an individual having no risk or low risk of the development of PE and optionally, contains one or more control antibodies or oligonucleotides. The control oligonucleotides or antibodies correspond to mRNA or proteins known to be present in the equal amount in a sample of an individual having a high risk of the development of PE as compared to the corresponding sample of an individual having no risk or low risk of the development of PE. Non-limiting examples of control oligonucleotides or antibodies include oligonucleotides or antibodies corresponding to β-actin, β-glucoronidase and GAPDH. Additional examples of control miRNAs or mRNAs depend on the tissue under examination. A person of ordinary skill in the art can determine control oligonucleotides appropriate for a particular assay and such embodiments are within the purview of the invention.

An aspect of the invention provides a kit, for example, a POC diagnostic device for assaying one or more histone or DNA modifying enzymes which can be used to identify the subject as having high risk of the development PE.

Epigenetic biomarkers of PE according to the invention also include the level of methylation of certain DNA loci in the genomic DNA of certain cells. Accordingly, an embodiment of the invention also provides a method of predicting the development of PE in a subject, the method comprising:

(a) determining the levels of methylation of one or more sites in the genomic DNA in:
  i) a test sample obtained from the subject, and
  ii) optionally a control sample;
(b) optionally obtaining one or more reference values corresponding to levels of methylation of the one or more sites, wherein the presence methylation of one or more sites in the genomic DNA:

at different levels in the test sample as compared to the control sample, or relative to the reference values indicates high risk of development of PE in the subject; and (c) identifying the subject as having high risk of developing PE based the levels of methylation of the one or more sites in the genomic DNA in the test sample and optionally, administering a therapy to the subject to treat and/or manage PE, or (d) identifying the subject as not having high risk of developing PE based the levels methylation of the one or more sites in the genomic DNA in the test sample and withholding the therapy to the subject to treat and/or manage PE.

As used herein, the term "level of methylation" as applied to a genomic site refers to whether one or more cytosine residues present in a CpG context have or do not have a methylation group. The level of methylation may also refer to the fraction of cells in a sample that do or do not have a methylation group on such cytosines. These cytosines are typically in the promoter region of the gene, though may also be found in the body of the gene, including introns and exons. The Beta-value is a ratio between methylated probe intensity and total probe intensities (sum of methylated and demethylated probe intensities). It is in the range of 0 and 1, which can also be interpreted as the percentage of methylation.

Various techniques are well known to a person of ordinary skill in the art to determine the level of methylation of one or more sites in the genomic DNA in a sample. Non-limiting examples of such techniques include bisulfite conversion, digestion by restriction enzymes followed by polymerase chain reaction (Combined Bisulfite Restriction Analysis, COBRA), direct sequencing, cloning and sequencing, pyrosequencing, mass spectrometry analysis or probe/microarray based assay. Certain techniques of determining methylation of genomic sites are described in Eads et al., Xiong et al., Paul et al., Warnecke et al., Tost et al., and Ehrich et al., the contents of which are herein incorporated in their entirety. Additional techniques for determining DNA methylation of one or more sites in the genomic DNA of a sample are well known to a person of ordinary skill in the art and such techniques are within the purview of the invention.

The reference value corresponding to levels methylation of one or more sites in the genomic DNA indicate the levels associated with no risk or low risk of the development of PE or high risk of the development of PE. As such, the reference values corresponding to levels of methylation of one or more sites in the genomic DNA may be indicative of the absence or presence of high risk of the development of PE. A reference value associated with no risk or low risk of the development of PE may be obtained based on samples obtained from women known to be free of PE. A reference value associated with high risk of the development of PE may be obtained based on samples obtained from women known to have PE. For example, tissues from a group of pregnant women can obtained during the first trimester and the levels methylation of one or more sites in the genomic DNA can be determined. The group of women can then be monitored for the development of PE. Reference values corresponding to the levels of methylation of one or more sites in the genomic DNA that are associated with low risk or no risk of the development of PE or high risk of the development of PE can be determined based on the presence of absence of PE in various women whose samples were analyzed. Additional examples of determining references values associated with no risk or low risk or high risk of the development of PE are well known to a person of ordinary skill in the art and such embodiments are within the purview of the invention.

The step of identifying the subject as having high risk or not having high risk of developing PE depends on the levels methylation of one or more sites in the genomic DNA in the test sample. For example, if the levels of methylation of one or more sites in the genomic DNA in the test sample are significant higher or lower than corresponding levels in the control sample, the subject is identified as having high risk of development of PE. Table 2 provides the Illumina ID, the corresponding sequences of the genomic sites and the level of methylation of the genomic sites in PE patients.

In one embodiment, a subject is identified as having high risk of the development of PE if the methylation of one or more genomic sites selected from SEQ ID NOs: 46-55 is increased in the genomic DNA of a test sample as compared to a control sample. In a specific embodiment, a woman is identified as having high risk of the development of PE if methylation of genomic site CYP19A1 (SEQ ID NO: 46) is increased in a sample, for example, buffy coat sample of blood, from the woman as compared to a control sample.

In another embodiment, a subject is identified as having high risk of the development of PE the methylation of one or more genomic sites selected from SEQ ID NOs: 2-45 is decreased in the genomic DNA of a test sample as compared to a control sample. A further embodiment of the invention provides a kit comprising reagents to carry out the methods of the current invention. The kit comprises reagents to conduct the assay to determine the levels methylation of certain sites in the genomic DNA in certain cells of a subject. The kit can include reagents for isolation of genomic DNA from a sample, reagents to treat the genomic DNA, for example, bisulfite treatment, specific primers to analyze the genomic sites of interests and reagents for PCR amplification of the sites of interest.

An aspect of the invention provides a kit, for example, POC diagnostic device for assaying methylation of one or more sites in the genomic DNA which can be used to identify the subject as having high risk of the development PE. PE arises from a complex interplay among several factors. Epigenetic mechanisms and miRNAs closely interact with each other, thereby creating reciprocal regulatory circuits which lead to gene regulation. The invention identifies novel interactive sets of epigenetic and miRNA biomarkers in the first trimester which can be used to predict the development of PE. Accordingly, one embodiment of the invention provides the methods of predicting, treating and/or managing PE in a subject; the method comprises determining two or more, for example, three, four, five, six, seven, eight, nine or ten biomarkers described herein to identify a subject as having a high risk of the development of PE. The multiple biomarkers can belong to the same class, for example, multiple miRNAs or multiple post-translational modifications of histone proteins; or the multiple biomarkers can be chosen from different classes, for example, a combination of miRNAs, post-translational modification of histones, histone or DNA modifying enzymes or methylation of certain genomic DNA sites. In an embodiment, the multiple biomarkers do not contain any biomarker from one or more classes described herein, e.g., the multiple biomarkers may not contain an miRNA, a post-translational modification of histone, a histone or DNA modifying enzyme or a methylation of a genomic DNA site.

Accordingly, an embodiment of the invention also provides a method of predicting the development of PE in a subject, the method comprising:

(a) determining the levels of two or more biomarkers selected from one or more of miRNA, post-translational modification of histones, histone or DNA modifying enzymes, methylation of certain genomic DNA sites in:

i) a test sample obtained from the subject, and ii) optionally a control sample;

(b) optionally obtaining one or more reference values corresponding to levels of one or more biomarkers, wherein the presence of two or more biomarkers:

at different levels in the test sample as compared to the control sample, or relative to the reference values indicates high risk of development of PE in the subject; and (c) identifying the subject as having high risk of developing PE based on the levels of two or more biomarkers in the test sample and optionally, administering a therapy to the subject to treat and/or manage PE, or (d) identifying the subject as not having high risk of developing PE based on the levels of two or more biomarkers in the test sample and withholding the therapy to the subject to treat and/or manage PE.

The combination of two or more biomarkers can be selected from the miRNAs, post-translational modification of histones, histone or DNA modifying enzymes, methylation of certain genomic DNA sites described earlier in this disclosure. In one embodiment, a subject is identified as having high risk of the development of PE if all of the analyzed biomarkers are significant different between the test sample and the control sample. In another embodiment, a subject is identified as having high risk of the development of PE if a pre-determined number of biomarkers out of the analyzed biomarkers are significant different between the test sample and the control sample. For example, if five biomarkers are analyzed, a subject can be identified as having high risk of the development of PE if more than three biomarkers are significant different between the test sample and the control sample.

In another embodiment, the comparison in the levels of two or more biomarkers between the test sample and the control sample is performed by as a combination of the two or more biomarkers, for example, by multivariable analysis. An example of multivariable analysis is multiple regression analysis. When the levels of two or more biomarkers are compared between the test sample and the control sample as a combination, the two or more biomarkers as a combination can be identified as significantly different between the two samples despite one or more of the multiple biomarkers not being different when considered individually.

In an embodiment, levels of four biomarkers, namely, miR-17, post-translational modification of H4 histone protein, amount of HDAC5 mRNA and/or protein and methylation of CYP19A1 site are determined. A subject is identified as having a high risk of the development of PE if the subject has increased miR-17, hyperacetylated H4 histone protein, decreased HDAC5 mRNA and/or protein and hypermethylated CYP19A1.

A further embodiment of the invention provides a kit, for example, POC diagnostic device, for identifying a subject as having high risk of PE based on the levels of two or more biomarkers. The POC device of the invention provides low-tech and cost-effective tool that still produces an accurate measurement, is portable, physically strong (compared to chip/sensing device), and simple to use. The kit can be used by virtually anyone, anywhere.

3-D printing technique can be used to manufacture the housing of the kit. Recycled materials, for example, recycled thermoplastic with added fibrous reinforcement, can be used to reduce the material cost and produce a light weight and unbreakable biomarker tool.

The invention provides a POC device capable of assaying miR-17, methylated CYP19A1, HDAC5 mRNA and acetylation of histone H4 in a sample, for example, a blood sample obtained from a subject. The sample can be treated before subject the sample to the analysis using the POC device.

The POC device can comprise of one or more locations for the introduction of the treated or untreated sample, which can be directed to two or more compartments, wherein each compartments is designed to assay different biomarker. For example, the POC device comprises of four compartments: one for assaying miR-17, one for assaying acetylation of H4 histone protein, one for assaying HDAC5 mRNA, and one for assaying methylation of CYP19A1.

Accordingly, a POC for reliable and rapid detection of biomarkers described herein is provided. In one embodiment, the POC utilizes an opto-fluidics-based platform for use as a biosensor.

In a certain embodiment, the POC incorporates functionalized colloidal nanoparticles trapped at the entrance to a nanofluidic channel providing a robust means for analyte detection at trace levels using surface enhanced Raman spectroscopy. The POC device can be used for sensitive detection of epigenetic modification in either blood or urine, is small and inexpensive, and can provide results in less than 15 minutes. Briefly, following the introduction of blood or urine, small molecules in the sample would compete with competing probes or aptamers depending on the molecule of interest. These probes will be already pre-bound to small molecule derivatives, and Raman reporter molecules attached on nanoparticles. The competition releases the gold particles which then aggregate at a nanochannel constriction downstream. To demonstrate the diagnostic potential of the system, a "gate" can be imposed; i.e., the lowest and highest value obtained from a healthy sample considered the healthy range. All values beyond this range can be assumed to be indicative of a change from normal conditions. As such, a low-cost, rapid, sensitive epigenetic diagnostic and prognostic tool for early detection of pre-eclampsia is provided.

To practice the methods described herein for identifying a subject as having high risk of the development of PE, control samples can be obtained from one or more of the following:

a) an individual belonging to the same species as the subject and not having PE, b) an individual belonging to the same species as the subject and known to have a low risk or no risk of developing PE, or c) the subject prior to becoming pregnant.

Additional examples of control samples are well known to a person of ordinary skill in the art and such embodiments are within the purview of the current invention.

In certain embodiments, the control sample and the test sample are obtained from the same type of an organ or tissue. Non-limiting examples of the organ or tissue which can be used as samples are placenta, brain, eyes, pineal gland, pituitary gland, thyroid gland, parathyroid glands, thorax, heart, lung, esophagus, thymus gland, pleura, adrenal glands, appendix, gall bladder, urinary bladder, large intestine, small intestine, kidneys, liver, pancreas, spleen, stoma, ovaries, uterus, skin, blood or buffy coat sample of blood. Additional examples of organs and tissues are well known to a person of ordinary skill in the art and such embodiments are within the purview of the invention.

In certain other embodiments, the control sample and the test sample are obtained from the same type of a body fluid. Non-limiting examples of the body fluids which can be used as samples include amniotic fluid, aqueous humor, vitreous humor, bile, blood, cerebrospinal fluid, chyle, endolymph, perilymph, female ejaculate, lymph, mucus (including nasal drainage and phlegm), pericardial fluid, peritoneal fluid, pleural fluid, pus, rheum, saliva, sputum, synovial fluid, vaginal secretion, blood, serum or plasma. Additional examples of body fluids are well known to a person of ordinary skill in the art and such embodiments are within the purview of the invention.

The methods described herein can be used to identify a subject as having high risk of the development of PE. In certain embodiments, the subject is a mammal. Non-limiting examples of mammals include human, ape, canine, pig, bovine, rodent, or feline.

In one embodiment, the methods described herein are used to identify a pregnant woman as having high risk of the development of PE. In another embodiment, the methods described herein are performed during the first trimester of pregnancy of a woman to identify the woman as having high risk of the development of PE.

Once a subject is identified as having high risk of the development of PE based on the methods described herein, the step of treating and/or managing PE includes one or more of:

a) administering medications to lower blood pressure: these medications, called antihypertensives, are used to lower blood pressure, b) administering corticosteroids, c) administering anticonvulsant medications, for example, magnesium sulfate, d) bed rest for the patient, e) hospitalization to perform regular non-stress tests or biophysical profiles to monitor the fetus' well-being and measure the volume of amniotic fluid, f) administering low-dose aspirin, g) administering calcium supplements, h) inducing delivery before natural labor is initiated.

As such, the invention provides that epigenetics and miRNA regulation provides very early manifestation of PE pathogenesis—one that presages the clinical onset of PE by a few months, for example, four to five months. In addition, the invention indicates a new paradigm of discovering interactive epigenetic biomarkers for prediction of PE at a very early stage, for example, during the first trimester. This study also paves new avenues to look for biomarkers in a unique perspective for other diseases. These epigenetic changes happen prior to gene expression, and they are often reversible, making them good candidates for therapeutic interventions.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Analysis of Samples to Determine MIRNA Biomarkers of PE

First trimester blood samples and uterine artery Doppler ultrasonography were obtained from 1007 women between 11 and 13 6/7 weeks of gestation. Epigenetic and miRNA profiling was performed on the serum or buffy coat samples from total of 51 controls and 17 severe PE cases. Cases and controls were closely matched with respect to age, sex, body mass index (BMI) and other relevant parameters (Table 3).

Figure 1B:
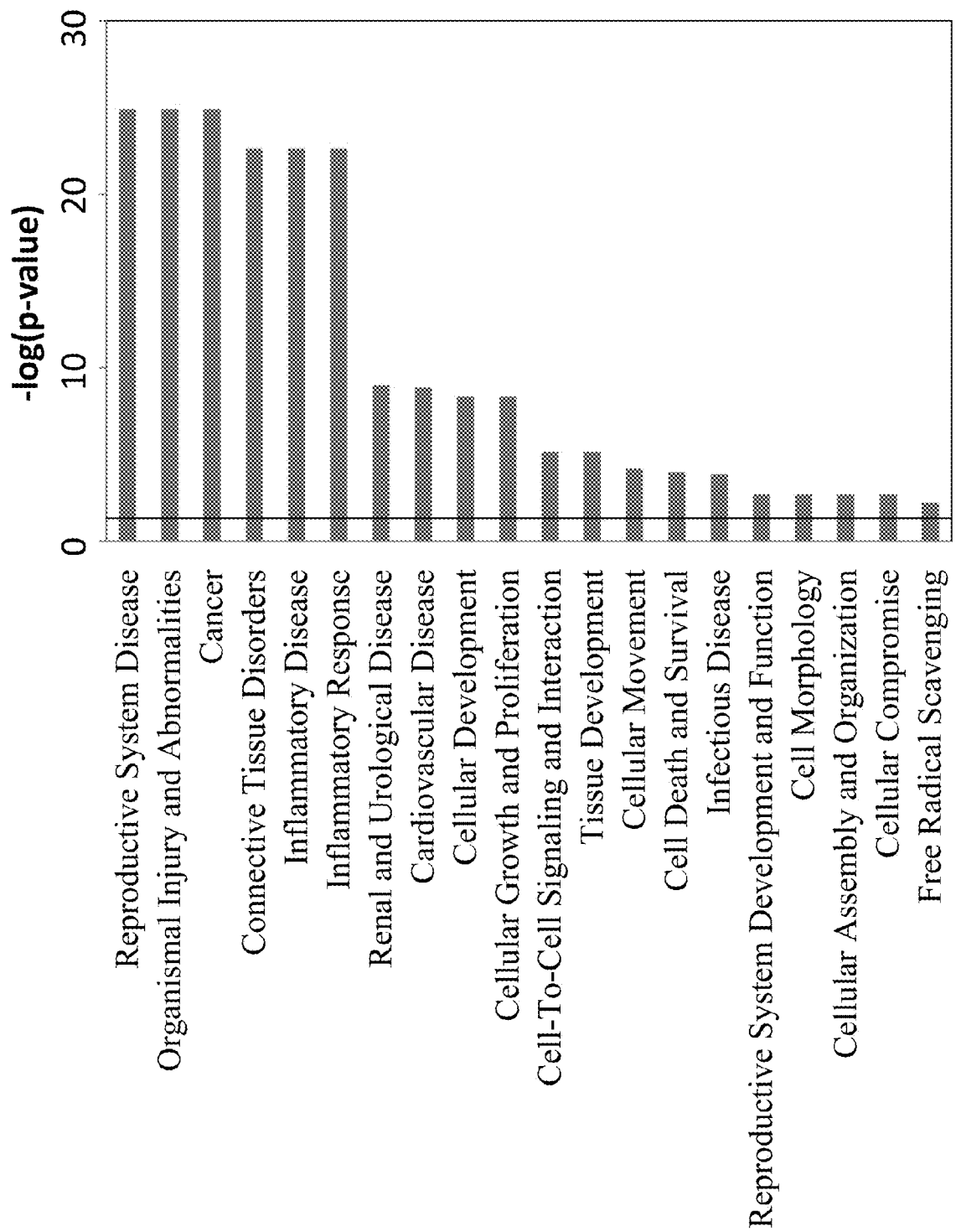
Figure 1C:
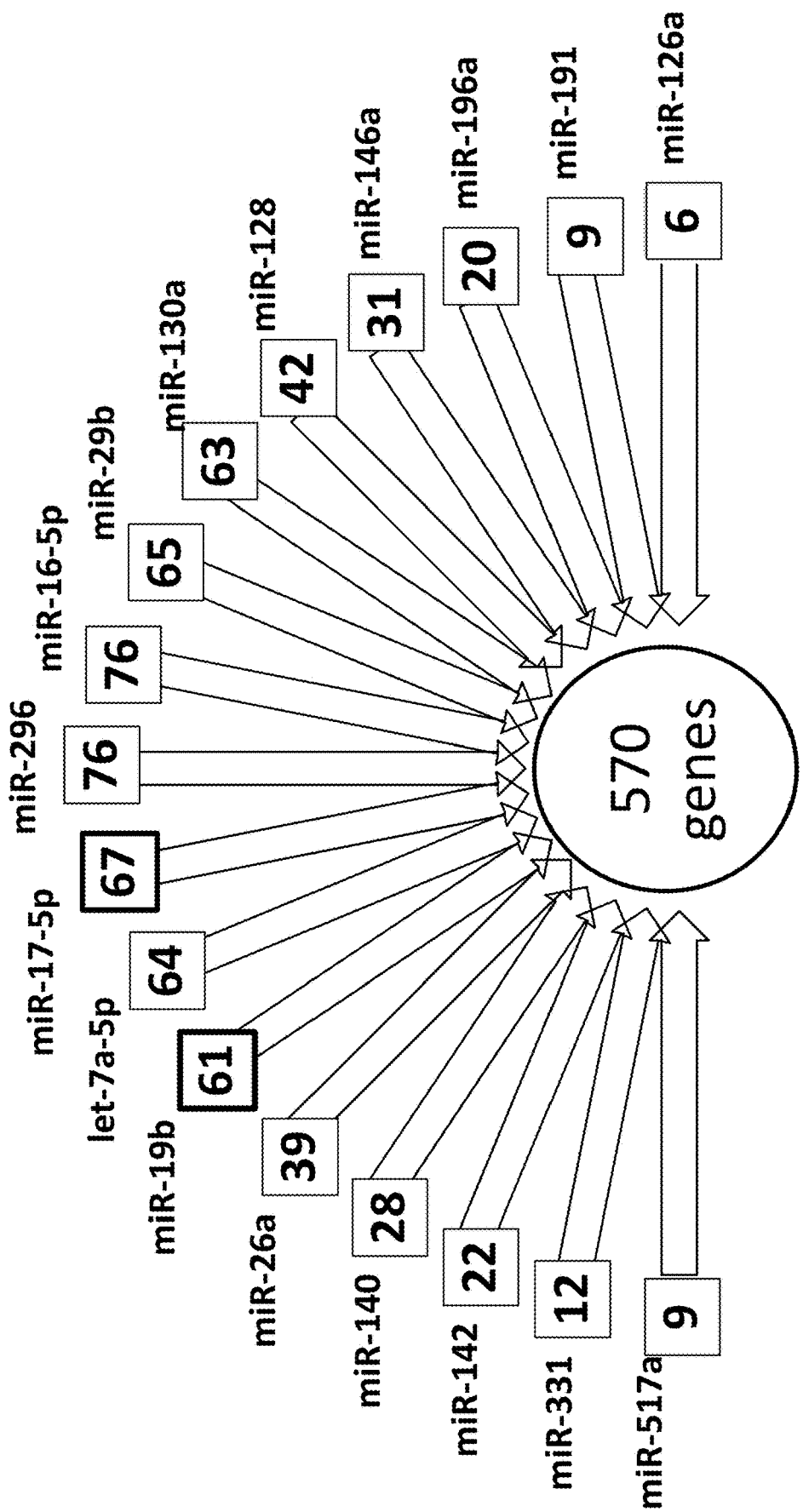

To compare PE women with controls, 381 miRNAs in 28 patients (C=14, PE=14) were examined. Expression profiles revealed 22 significantly upregulated miRNAs which are shown to be involved in reproductive system disease ($p<0.02$) (FIGS. 1A, 1B, 1C, Table 4). Out of these 22 miRNAs, namely, 7c, 93, 128a, 140-3p, 142-3p, 146b, 15a, 196b, 331-5p, 886-5p) are identified as novel biomarkers of PE.

Upregulation of certain miRNAs, namely, 17, 26a, 130b, 7a, 29a, 517a, 191 & 296 in the third trimester in the serum or in the placenta is reported. Conversely, Wang et al. (2008) and Hong et al. (2014) showed that miR-126 functions as a pro-angiogenic factor in rat placenta and is decreased in endothelial progenitor cells in term placenta of PE patients. However, evidence showed that miR-126 functions as a pro-angiogenic factor in rat placenta and is decreased in endothelial progenitor cells in term placenta of PE patients.

Figure 1D:
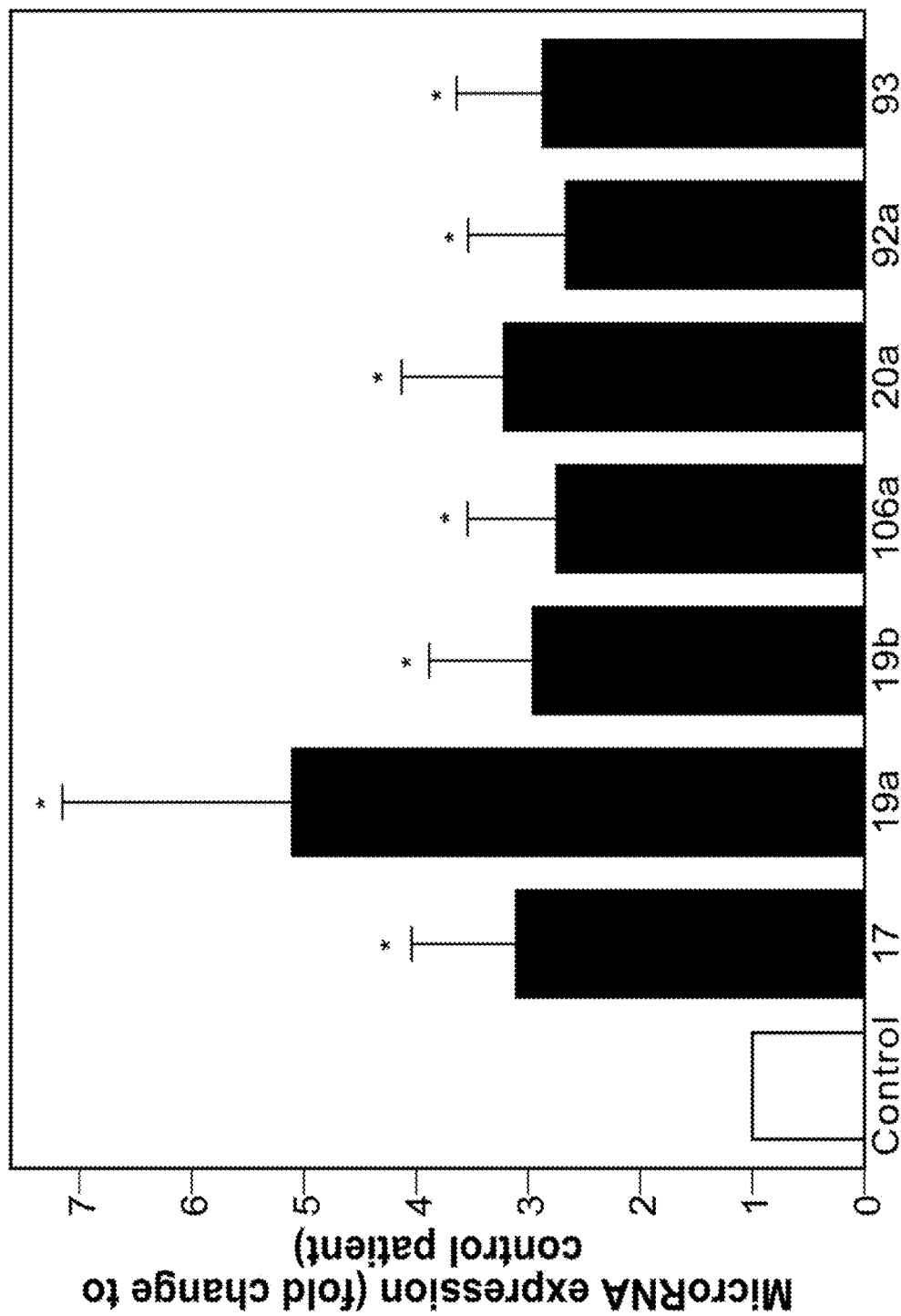

Several groups showed that the miR-17 cluster (miR-17, miR-18a, miR-19a, miR-20a, miR-19b-1, and miR-92a-1) and its paralog, the miR-106a cluster (miR-106a, miR-18b, miR-20b, miR-19b-2, miR-92a-2, and miR-363) are significantly increased in term placentas of PE women. This is consistent with the results at 11-13 weeks (FIG. 1D) provided in the instant invention. In addition, the miR-17~92 cluster has been established as an anti-angiomiR and therefore can lead to inhibition of angiogenesis which is a hallmark of PE.

Example 2—Analysis of Samples to Determine Post-Translational Modifications of Histones as Biomarkers of PE Post-translationally modified (PTM) histones in buffy coat samples were characterized using reverse-phase liquid chromatography mass spectrometry. The profiles showed several species that corresponded in mass to core and linker histones variants and their PTM isoforms (data not shown, Su et al. (2007)). Multiple PTMs were measured; however, the core histones (H3, H2A, H2B) showed complicated spectra due to the presence of multiple variants and a high degree of PTMs, in particular acetylation and methylation. ELISA study showed no changes in H2A in PE serum. Histone H4 showed unique spectra as H4 does not have sequence variants (uncomplicated by multiple variants, unlike other histones).

In H4 spectra, the most abundant species was observed at 11,306 Da which correspond in mass with dimethylation (DiMe) and N-terminal acetylation (N-Ac) of H4 (Su et al. (2007)). The next most abundant peaks, 11,348 Da and 11,390 Da, correspond to additional H4 acetylation (Su et al. (2007)). Ratio of relative abundance of 11349/11307 peak area demonstrated the H4 acetylation levels in patients with and without PE.

The statistical power was limited by small sample size (PE=8, C=8); however, more H4 acetylation was observed in PE patients (p=0.09) compared to controls (FIG. 2A(1) and FIG. 2A(2)). Based on previous reports and peptide mass mapping and tandem mass spectrometry, the 11,306 Da peak was identified as N-Ac+K20DiMe; the 11,348/9 Da peak was identified as N-Ac+K16Ac+K20DiMe; and the 11390/1 Da peak was identified as N-Ac+K16Ac+K12Ac+K20DiMe.

The evidence suggests that histone acetylation may mediate development of chronic inflammation by modulating the expression of pro-inflammatory cytokine TNF-α and interleukins, and activation of the transcription factor NF-κB. These molecules are constitutively produced by a variety of cells under chronic inflammatory conditions, which in turn leads to the development of major diseases such as PE. The invention provides that H4 acetylation is associated with PE.

Figure 2B:
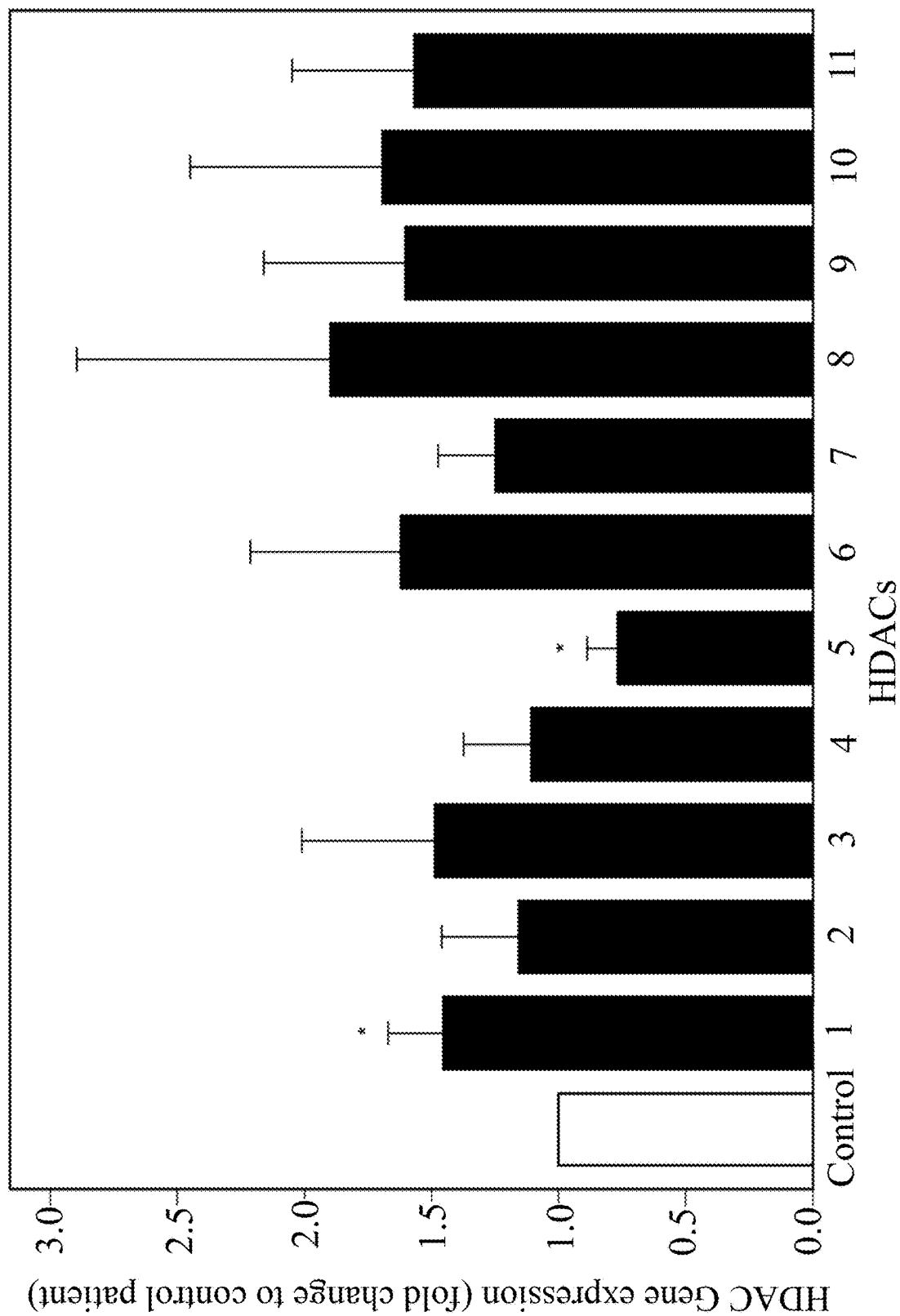
Figure 3:
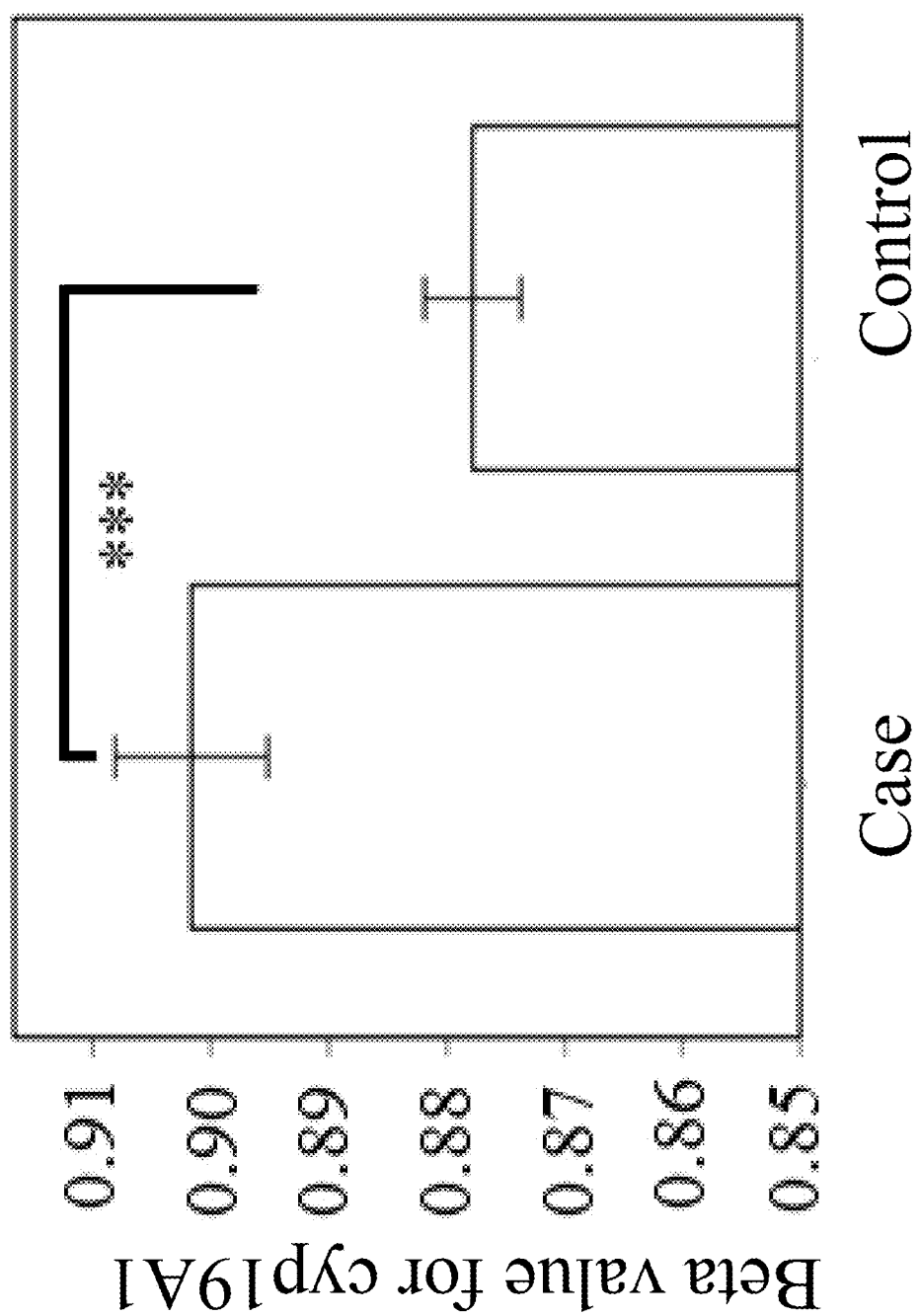
FIG. 3. Significant hypermethylated CYP19A1 gene: Methylation status of CYP19A1 was profiled in Infinium HumanMethylation450 assay. The bar graph shows the hypermethylated status of CYP19A1 in 12 PE cases and 24 controls. Genome studio analysis profiled the methylation level as a beta value. All error bars, S.E.M.***$p<0.001$ were determined by two-way t test. The p-value was corrected for multiplicity using false discovery rate method ($p$-value$<0.016$).
Figure 4:
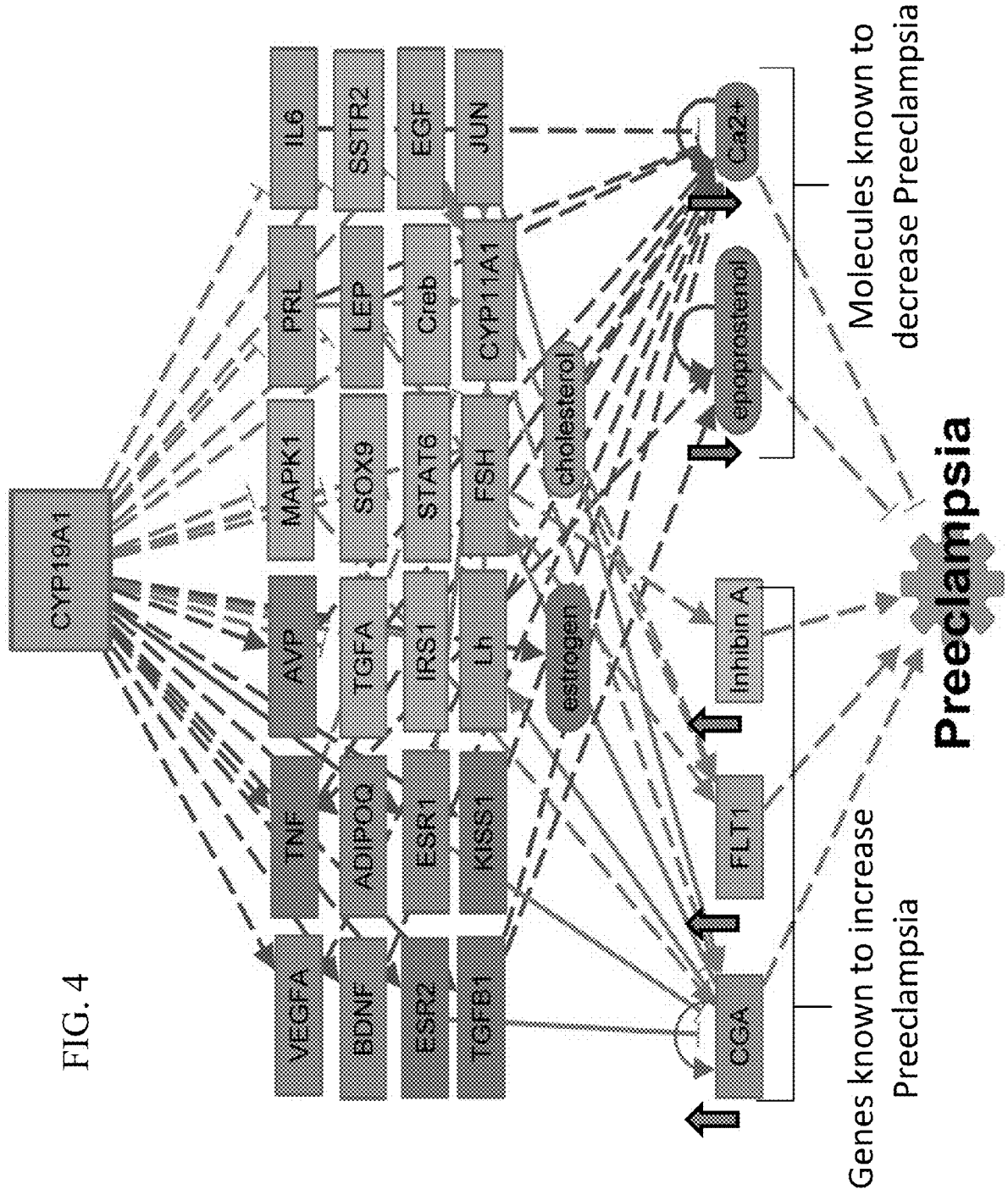
FIG. 4. Role of CYP19A1 in the development of PE: Pathway analysis was carried out to analyze the relationship between CYP19A1 and genes associated with PE in IPA database. The 'Path Explorer' tool was used to generate the connections between CYP19A1 and the genes/molecules associated with PE. Downregulated CYP19A1 was overlaid in the predicted activity analysis using IPAs 'Molecule Activity Predictor' tool. Known genes in orange boxes depict upregulation and genes in blue boxes indicate downregulation. Rectangles represent genes and rounded rectangles are assigned for endogenous molecules.

Example 3—Analysis of Samples to Determine Histone or DNA Modifying Enzymes as Biomarkers of PE The expression levels of 81 epigenetic genes which are involved in histone modifications and DNA methylation was measured. Two of the eleven HDACs were significantly altered with no changes in HAT expression ($p<0.05$) (FIG. 2B). Even though increased HDAC1 did not correspond with hyperacetylation, this may reflect specific actions of individual HDACs. The decrease in HDAC5 has been shown to increase H4 acetylation in an unrelated study. This corresponds well to PE patients' hyperacetylated histone H4 profile. Thus, modulation of HDAC or histone acetylation levels may represent an underlying cause/consequence of cytokine dysregulation in PE.

In addition to the HDACs, aurora kinase A (AURKA), aurora kinase C (AURKC), and protein arginine methyltransferase 8 (PRMT8) were significantly altered ($p<0.05$).

Example 4—Analysis of Samples to Determine Level of Methylation of Genomic DNA Sites as Biomarkers of PE DNA methylation was determined using Comprehensive High-throughput Arrays for Relative Methylation (CHARM) [6 Control (C) and 6 PE patients]. Significant ($p<0.05$) hypomethylation was associated with 81 genes in PE patients with an average methylation difference of 37.5% (min: 30%, max: 45%).

Using Infinium HumanMethylation450 assay in 36 samples (PE=12, C=24), 5904 significant CpG islands ($p<0.05$) were identified to be associated with PE. Out of 5904 islands, 86 CpG islands were significantly methylated (adjusted p-values, corrected for multiplicity-q=0.01). Of the 86 sites, 54 were associated with genes (10 hypermethylated & 44 hypomethylated, Table 2). Repetition of the same genes was not observed when the results of CHARM and Infinium assays were compared; however, repetitions were observed in the same families (e.g., solute carrier (SLC) family, zinc finger protein (ZNF) family), related upstream and downstream regulators, and pathways (Table 5).

A large portion of these gene sets do not have a known function but several have been reported in the context of PE or a function related to PE (e.g. angiogenesis, invasion, migration etc.). Using TARGETSCAN, mirBase and IPA, several of these genes are discovered as targets of the significantly upregulated miRNAs. In epigenetic gene expression assay changes in DNA methyl transferase were not observed. This lack of correlation may indicate that DNA methyltransferase (DNMT) activity might be the primary route, or frequency of DNA methylation may result from other mechanisms besides expression of DNMT since both hyper and hypo methylation are observed.

Hypermethylated CYP19A1 is provided as a first trimester PE biomarker. The synthesis of estrogens from $C_{19}$ steroids is catalyzed by aromatase P450 (P450arom, product of the hCYP19A1 gene) and the ability of the human placenta to synthesize estrogens is vastly increased after the ninth week of gestation. Placental aromatase deficiency has been found in PE. In addition, biologically active estrogens and their metabolites formed by placental aromatase may also enhance angiogenesis and uteroplacental blood flow and reduce systemic vascular resistance. The scenario is mostly hampered in PE. Since the blood was collected after nine weeks of gestation, decreased CYP19A1 was expected in the patients who develop PE. Epigenetic modifications presage any gene expression and pathophysiology. A hypermethylated gene leads to decreased gene expression which is expected to be evident at later gestation. Upregulated mir-17 and -106a cluster was associated with decreased expression of CYP19A1 in term placenta (correspondence of decreased estrogen levels with increasing severity of PE). These miRNA clusters inhibited trophoblast differentiation by repressing CYP19A1. miR-17 is also predicted to target HDAC5 and subsequently a decrease in HDAC5 has been shown to increase H4 acetylation. In addition, target analysis has shown that miR-17 and other miRNAs target several well-known PE markers, PAPPA, VEGF, MMP, etc. Evidence also supports a role to these four markers in other PE pathologies (e.g. hypoxia, oxidative stress, inflammatory response, invasion, placental insufficiency). Therefore, these four interacting biomarkers underline the robustness of this analysis and also strengthen the previously published work and might serve as novel predictors of PE.

PE arises from a complex interplay among several factors. The invention shows that epigenetic mechanisms and miRNAs closely interact with each other, thereby creating reciprocal regulatory circuits which lead to gene regulation. The invention identifies novel interactive sets of noninvasive epigenetic and miRNA biomarkers in the first trimester which have a strong potential to predict the future development of PE.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 2

Illumina ID, related genomic sequences and the level of methylation of the genomic sites in PE patients compared to control

| Illumina ID* | Gene Name | Methylation status in PE Patients | Sequene of the genomic site | AlleleA_ProbSeq** | AlleleB_ProbeSeq*** | Ch. No. | Strand Orientation**** | UCSC_RefGene_Accession |
|---|---|---|---|---|---|---|---|---|
| cg00073460 | ZC3H12D | hypo | CGGTACTCACAG CTGGACACAAAC ATAGCTTGCAGG AGGAAGAGTGTC AG (SEQ ID NO: 2) | TCTAACACTCTTC CTCCTACAAACTA TATTTATATCCAA CTATAAATACC (SEQ ID NO: 116) | | 6 | F | NM_207360 |
| cg00522231 | ITGB1BP1 | hypo | CGTCCGCCAGGG AAGCTGTCAGGG ATTATCTGCGGTT CCTGAGTAGCTG A (SEQ ID NO: 3) | TCAACTACTCAAA AACCACAAATAA TCCCTAACAACTT CCCTAACAAACA (SEQ ID NO: 117) | TCAACTACTCA AAAACCGCAA ATAATCCCTAA CAACTTCCCTA ACGAACG (SEQ ID NO: 170) | 2 | R | NM_004763; NM_022334 |
| cg00616135 | LACTB | hypo | TTAGTTTTGGATC CTCAACTTCTGGA ACAGCGCAGGGC ACACAGTAGACG (SEQ ID NO: 4) | CTTAATTTTAAAT CCTCAACTTCTAA AACAACRCAAAA CACACAATAAAC (SEQ ID NO: 118) | | 15 | F | NM_032857; NM_171846 |
| cg01844274 | SYNE1 | hypo | GTTACTCTTCCAG GGTGCACACAAG AGGCAATGAAGC CCAGGAATTAC G (SEQ ID NO: 5) | TATTACTCTTCCA AAATACACACAA AAACAATAAAA CCCAAAAATTA C (SEQ ID NO: 119) | | 6 | R | NM_182961; NM_033071 |
| cg02203224 | ARL6IP4; OGFOD2 | hypo | CGCTGAAGCCCC ATTCCAGACCCTG CTTCTGACAAACC TGAACTAAGGCA (SEQ ID NO: 6) | CTACCTTAATTCA AATTTATCAAAA ACAAAATCTAAA ATAAAACTTCAA C (SEQ ID NO: 120) | | 12 | R | NM_018694; NM_001002251; NM_024623; NM_016638; NM_001002252 |
| cg02313130 | CAPN8 | hypo | CGAGATGGGAAG ATTATCCTGACCC TAAATACACAAG TGTCCTAAGAGG A (SEQ ID NO: 7) | TTCCTCTTAAAAC ACTTATATATTTA AAATCAAAATAA TCTTCCCATCTC (SEQ ID NO: 121) | | 1 | F | NM_001143962 |

TABLE 2-continued

Illumina ID, related genomic sequences and the level of methylation of the genomic sites in PE patients compared to control

| Illumina ID* | Gene Name | Methyl-ation status in PE Patients | Sequene of the genomic site | AlleleA ProbeSeq** | AlleleB ProbeSeq*** | Ch. No. | Strand Orien-tation**** | UCSC_RefGene_Accession |
|---|---|---|---|---|---|---|---|---|
| cg02452209 | PTPRN2 | hypo | CGGCCGCGGCTCT GATGCTTTGCAG GCGGCATTGTGTC ACTGATTCACT (SEQ ID NO: 8) | AATAAATCAATA ACACATACCAC CTACAAAACAT CAAAACCACAA CA (SEQ ID NO: 122) | AATAAATCAAT ACACATACC GCCTACAAAAA CATCAAAACCG CGACCG (SEQ ID NO: 171) | 7 | R | NM_002847; NM_130842; NM_130843 |
| cg02557110 | SLC12A7 | hypo | CGCTGGCTCTGCT TCCATTCCTGAAG TCTCAGCTCTCC CAGGGTGTCAG (SEQ ID NO: 9) | TCTAACACCCTAA AAAAACCTAAAA CTTCAAAAATAA AAACAAAACCAA C (SEQ ID NO: 123) | | 5 | R | NM_006598 |
| cg03484267 | KLF7 | hypo | CGGCCCCGCAG CCGTCACGGCTGC TGCAGCTGTTGCG ACCCCTCCCACC (SEQ ID NO: 10) | AATAAAAAAAT CACAACAACTAC AACTACCAAAAA AACTACAAAAAC CA (SEQ ID NO: 124) | AATAAAAAAA ATCGCAACAAC TACAACAACCG TAACGACTACG AAAACCG (SEQ ID NO: 172) | 2 | F | NM_003709 |
| cg04546999 | SPRR1A | hypo | CAGTGCCAAAAA ATATCAGGTGGT GTTCATCAAAAA AGCTGAGCCAAC CG (SEQ ID NO: 11) | CCAATACCAAAA AATATCAAATAA TATTCATCAAAAA AACTAAAACCAA C (SEQ ID NO: 125) | | 1 | R | NM_005987 |
| cg05337441 | APOB | hypo | CGCCCCCCATCCT GAGCCTGCAGGG GCCGCCAGCTGG TCCAATCCCCCA (SEQ ID NO: 12) | ATAAAAAATTA AACCAACTAACR ACCCCTACAAACT CAAAATAAAAAA C (SEQ ID NO: 126) | | 2 | F | NM_000384 |
| cg05747459 | CNKSR2 | hypo | TTGTCTCCAGCTA GAGGGGCGCGGA GCGGCCAGAGAG CTAGAGGGCAGC G (SEQ ID NO: 13) | TTATCTCCAACTA AAAAACACAAA ACAACCAAAAA CTAAAAAACAA A (SEQ ID NO: 127) | TTATCTCCAAC TAAAAAACGC GAAACGACCA AAAACTAAA AAACACG (SEQ ID NO: 173) | X | R | NM_001168649; NM_001168648; NM_014927; NM_001168647 |

TABLE 2-continued

Illumina ID, related genomic sequences and the level of methylation of the genomic sites in PE patients compared to control

| Illumina ID* | Gene Name | Methylation status in PE Patients | Sequene of the genomic site | AlleleA_ProbeSeq** | AlleleB_ProbeSeq*** | Ch. No. | Strand Orientation**** | UCSC_RefGene_Accession |
|---|---|---|---|---|---|---|---|---|
| cg05775542 | NAPG | hypo | GAACTGCCACAA AGTCATAGCTTCT TTTTTTTTCTTAA GATAGGTCTCG (SEQ ID NO: 14) | AAAACTACCACA AAATCATAACTTC TTTTTTTTCTTAA AATAAAATCTC (SEQ ID NO: 128) | AAAACTACCACA AAATCATAACTTC TTTTTTTTCTTAA AATAAAATCG | 18 | F | NM_003826 |
| cg06109379 | IQSEC3 | hypo | GTGGAGTCACCC GGCCACACTCGG GTGGGGCCCAGG AATGGACGGGGG CG (SEQ ID NO: 15) | ATAAAATCACCC AACCACACTCAA ATAAAACCCAAA AATAACAAAAA CA (SEQ ID NO: 129) | ATAAAATCACCC CGACCACACTC GAATAAACCC AAAATAAAAC GAAAACG (SEQ ID NO: 174) | 12 | F | NM_001170738; NM_015232 |
| cg07532159 | LAMA2 | hypo | ATCTCATGGTTCA CCGTTTTTTAAGC CCGTCGGAAAAG CGCAGTATTCCG (SEQ ID NO: 16) | ATCTCATATATTCA CCATTTTTTAAAC CCATCAAAAAAA CACAATATTCCA (SEQ ID NO: 130) | ATCTCATATAATT CACCGTTTTT AAACCCGTCGA AAAACGCAAT ATTCCG (SEQ ID NO: 175) | 6 | R | NM_001079823; NM_000426 |
| cg08035151 | LSM2 | hypo | CGAGGAAACTGA GGCTTAGATCAG CTATACCACTTGT TCAAGTCTACAA A (SEQ ID NO: 17) | TTTTATAAACTTA AACAAATAATAT AACTAATCTAAA CCTCAATTTCCTC (SEQ ID NO: 131) | | 6 | R | NM_021177 |
| cg08944086 | ADARB2 | hypo | CGGTCCCTCCCT CCAGCGTCCCGCT CAGCTCCAGCAG CCAGGAGCCCGC (SEQ ID NO: 18) | ACAAACTCCTAA CTACTAAAACTA AACAAAACACTA AAAAAAAATAAAAC CA (SEQ ID NO: 132) | ACGAACTCCTA ACTACTAAAAC TAAACGAAACG CTAAAAAAATA AAACCG (SEQ ID NO: 176) | 10 | F | NM_018702 |
| cg09268718 | SCARF1 | hypo | CGCCCCGCCCGCT CACAGGTCTCCGC GCAGCCTCGCTCA CCTGTGTCCGC (SEQ ID NO: 19) | ACAAACACAAAT AAACAAAACTAC ACAAAAAACTAT AAACAACAAAA CA (SEQ ID NO: 133) | ACGAACACAA ATAAACGAAAC TACGCGAAAAC CTATAAACGAA CGAAACG (SEQ ID NO: 177) | 17 | F | NM_145352; NR_028075; NM_003693; NR_028076; NM_145350 |

TABLE 2-continued

Illumina ID, related genomic sequences and the level of methylation of the genomic sites in PE patients compared to control

| Illumina ID* | Gene Name | Methylation status in PE Patients | Sequence of the genomic site | AlleleA_ProbeSeq** | AlleleB_ProbeSeq*** | Ch. No. | Strand Orientation**** | UCSC_RefGene_Accession |
|---|---|---|---|---|---|---|---|---|
| cg09276451 | VASN; CORO7 | hypo | CCTCATAGGCATC TGGGCTGTGACG CTTAGGATTCCTA AATAGTCTCTG (SEQ ID NO: 20) | ACCTCATAAACAT CTAAACTATAACR CTTAAAATTCCTA AATAATCTCTC (SEQ ID NO: 134) | | 16 | R | NM_138440; NM_024535 |
| cg12184421 | CD247 | hypo | CGCTTAGTGTCCT GAGCATCTGTGG GAAGCTGACACA GCCTCACTCCTGC (SEQ ID NO: 21) | AACAAAAATAAA ACTATATCAACTT CCCACAAATACTC AAAACACTAAAC (SEQ ID NO: 135) | | 1 | F | NM_198053; NM_000734 |
| cg13253636 | PCDH21 | hypo | TGTTACAGTTCTC ATTGGGAGGTTTC TCTTTGAGCATGA ACTTGGTAGCG (SEQ ID NO: 22) | TTATTACAGTTCT CATTAAAAAATTT CTCTTTAAACATA AACTTAATAAC (SEQ ID NO: 136) | | 10 | F | NM_033100 |
| cg13064046 | SCAMP5 | hypo | CGGCTCACTGCA AGCTCCGCCTCGG GAAAACATGGGG GTGGTTCCACCTC (SEQ ID NO: 23) | AAAAATAAAACC ACCCCCATATTTT CCCRAAACRAAA CTTACAATAAACC (SEQ ID NO: 137) | | 15 | R | NM_138967 |
| cg13259177 | RASA3 | hypo | GGGGGCCCGGCT GATGGGGACCCG GCTGATGGGGG CCGGAAGACAA CG (SEQ ID NO: 24) | AAAAACCCAACT AATAAAAACCCA ACTAATAATAAA CCAAAAAAACAA CA (SEQ ID NO: 138) | AAAAACCCGAC TAATAAAAACC CGACTAATAAAA AAACCGAAAAA AACACG (SEQ ID NO: 178) | 13 | R | NM_007368 |
| cg14741114 | TTTY15 | hypo | CGCCGCGACCTG CGACCCTCCAAG ACCCACCCCCGC CAAGCCGCCCC C (SEQ ID NO: 25) | AAAACAAAACTTG AACAAAATAAA ATCTTAAAAAATC ACAAATCACAAC A (SEQ ID NO: 139) | AAAACGAAACTT AACGAAAAATA AAATCTTAAAA AATCGCAAATC GCGACG (SEQ ID NO: 179) | Y | R | NR_001545 |
| cg15930811 | C1orf151 | hypo | CGCCATTTTATAT ATGGGACTTGAG CATCCTGCATTTT GGTAACTGCGAG (SEQ ID NO: 26) | TCTCRCAATTACC AAAATACAAAAT ACTCAAATCCCAT ATATAAAATAAC (SEQ ID NO: 140) | | 1 | R | NM_001032363 |

TABLE 2-continued

Illumina ID, related genomic sequences and the level of methylation of the genomic sites in PE patients compared to control

| Illumina ID* | Gene Name | Methylation status in PE Patients | Sequene of the genomic site | AlleleA_ProbSeq** | AlleleB_ProbSeq*** | Ch. No. | Strand Orientation**** | UCSC_RefGene_Accession |
|---|---|---|---|---|---|---|---|---|
| cg16027847 | WDR27 | hypo | CGGGACCTGCAG CCTGACATGCCCG AGCCCCACCCCTG CCACTCCCGTGA (SEQ ID NO: 27) | TCACAAAATAA CAAAATAAAC TCAAACATATCA AACTACAAATCC CA (SEQ ID NO: 141) | TCACGAAAATA ACAAAATAAAC AACTCGAACAT ATCAAACTACA AATCCCG (SEQ ID NO: 180) | 6 | F | NM_182552 |
| cg16627211 | AP3S1 | hypo | CGCTACTGCAGC ATAAATTAGCTCA TCCTGACTGATAA CAAAAGGGATAT (SEQ ID NO: 28) | AATATCCCTTTA TTATCAATCAAAA TAAACTAATTTAT ACTACAATAAC (SEQ ID NO: 142) | | 5 | R | NM_001284 |
| cg16887334 | OXT | hypo | CGCACTCGGCCTG ACCCACGGCGAC CCTCTGTGACCAA TCATACTACCAA (SEQ ID NO: 29) | TTAATAATATAAT TAATCACAAAAA ATCACCATAAATC AAACAAATACA (SEQ ID NO: 143) | TTAATAATATA ATTAATCACAA AAAATCGCCGT AAATCAAACCG AATACG (SEQ ID NO: 181) | 20 | F | NM_000915 |
| cg17293719 | ZNF645 | hypo | AACCCATTATCA CGTCATTAGGATC CAAGTTTCGGCTC ACAAGGGACCG (SEQ ID NO: 30) | TAACCCATTATCA ACRTCATTCRACT CCAATTTCRACT CACAAAAACC (SEQ ID NO: 144) | | X | F | NM_152577 |
| cg17568421 | LOC10018 8947 | hypo | CGGCCAGTTCCTT CTGGACACCTTGT CTGTCCTTGAGCT ATCATGTAATC (SEQ ID NO: 31) | AAATTACATAAT AACTCAAAAACA AACAAAATATCC AAAAAAAACTAA CC (SEQ ID NO: 145) | | 10 | R | NR_024467 |
| cg17695512 | OR10AG1 | hypo | TCCTGTAGTAATT GGGGAAACATGC CAAATTTTCCTT TTACCCTTTTAC TGCCCTTTTGCG (SEQ ID NO: 32) | TTCCTATAATAAT TAAAAAACATA CCAAATTTTCCTT TTACCCTTTTAC (SEQ ID NO: 146) | | 11 | F | NM_001005491 |

TABLE 2-continued

Illumina ID, related genomic sequences and the level of methylation of the genomic sites in PE patients compared to control

| Illumina ID* | Gene Name | Methylation status in PE Patients | Sequence of the genomic site | AlleleA_ProbeSeq** | AlleleB_ProbeSeq*** | Ch. No. | Strand Orientation**** | UCSC_RefGene_Accession |
|---|---|---|---|---|---|---|---|---|
| cg19394169 | RPTOR | hypo | CGCCGCACCTCCA CTTCTGCCCATGC TTGTCCTGTGACC CTCGTGTCAT (SEQ ID NO: 33) | ATAACCACAAAA ATCACAACAAAA ACATAAACAAAA ATAAAATACAA CA (SEQ ID NO: 147) | ATAACCACGAA AATCACAACAAAC AAACATAAACA AAAATAAAAAT ACGACG (SEQ ID NO: 182) | 17 | F | NM_001163034; NM_020761 |
| cg20765408 | PARP4 | hypo | TCCACCTACACCA ATGGTTTATGGAG CAGCCAAGAGTT TGTGAGGAGGCG (SEQ ID NO: 34) | TTCCACCTACACC AATAATTTATAAA ACACCAAAAAT TTATAAAAAAAC (SEQ ID NO: 148) | | 13 | F | NM_006437 |
| cg22559596 | INPP5A | hypo | CGGGGCTGTCTCT CACTGGCAGGGG CCACTCTCCGTG GACCGACCTGAG (SEQ ID NO: 35) | CTCAAATCAATCC ACAAAAAATAA CCCTACCAATAA AAAACAACCCA (SEQ ID NO: 149) | CTCAAATCGAT CCACGAAAAA ATAACCCTAC CAATAAAAAAC AACCCG (SEQ ID NO: 183) | 10 | R | NM_005539 |
| cg26086288 | SLC9A3 | hypo | GACGCGGGGCT GCAAGAACACGG GGAGACGTGTC CCCTTGGGTTCCC G (SEQ ID NO: 36) | AACACAAAACT ACAAAAAACA AAAACATATAC CCCTTAAATTCCC A (SEQ ID NO: 150) | AACGCGAAAA CTACAAAAACA CGAAAAAACGT ATACCCCTTAA ATTCCCG (SEQ ID NO: 184) | 5 | F | NM_004174 |
| cg26993132 | CDH15 | hypo | CGGCTCCTGCCAC CCCGACTCCCCC ATCTGGAGACAG TGGTGGGGGAG (SEQ ID NO: 37) | CTCCCCCCACCAC TATCCAATAA AAAATCAAAAA TAACAAAACCA (SEQ ID NO: 151) | CTCCCCCCACC ACTATCTCCAA ATAAAAAATC GAAAATAAACA AAAACCG (SEQ ID NO: 185) | 16 | F | NM_004933 |
| cg27554551 | VASN; CORO7 | hypo | GCCAGAAGTCCA CCCCAGGGCCTCT GCGGCCCTGGAG AGGCAGGATGGC G (SEQ ID NO: 38) | ACCAAAAAATCCA CCCCAAAACCTCT ACACCCTAAAA AAACAAAATAAC A (SEQ ID NO: 152) | ACCAAAAATCC ACCCCAAAACC TCTACGACCCT AAAAAAACAA AATAACG (SEQ ID NO: 186) | 16 | F | NM_138440; NM_024535 |

TABLE 2-continued

Illumina ID, related genomic sequences and the level of methylation of the genomic sites in PE patients compared to control

| Illumina ID* | Gene Name | Methylation status in PE Patients | Sequence of the genomic site | AlleleA ProbeSeq** | AlleleB ProbeSeq*** | Ch. No. | Strand Orientation**** | UCSC RefGene Accession |
|---|---|---|---|---|---|---|---|---|
| cg00713642 | IGBP1 | hypo | TATTGCTTCTGCA CCAATATAAAGT AAAAAATTCTAA GACAAGCCATCG (SEQ ID NO: 39) | ATATTACTTCTAC ACCAATATAAAA TTAAAAATTCTA AACAAACCATC (SEQ ID NO: 153) | | X | F | NM_001551 |
| cg02961385 | CRTC1 | hypo | AGGACGGAGCAG CAACGTGGGCCA GGGCAGGGGTGC AGGAAAGCAACG CG (SEQ ID NO: 40) | AAAACAAAACAA CAACATAAACCA AAACAAAAATAC AAAAAAACAACA CA (SEQ ID NO: 154) | AAAACGAAAAC AACAACGTAAA CCAAAACAAA AATACAACAA AACAACGCG (SEQ ID NO: 187) | 19 | F | NM_015321; NM_001098482 |
| cg21765032 | BRUNOL5 | hypo | TCTTGAAGCATCA CCCCACCTGGGG AGGGTTTGGAGC ATGAAGTGGGCC G (SEQ ID NO: 41) | CTCTTAAAACATC ACCCCACCTAAA AAAATTTAAAA CATAAAATAAAC C (SEQ ID NO: 155) | | 19 | F | NM_021938 |
| cg25749512 | ACVRL1 | hypo | TCAGTGGGCCCTT CCTTCGGGCGGA CCCAGAGTCAC CGCAGAGTGGTC G (SEQ ID NO: 42) | TCAATAAACCCTT CCTTCAAACAAA CCCCAAAATAA CACAAAATAATC A (SEQ ID NO: 156) | TCAATAAACCC TTCCTTCGAAC GAACCCCAAAA TCACCGCAAAA TAATCG (SEQ ID NO: 188) | 12 | R | NM_000020 |
| cg00295339 | BANP | hypo | CGGCCCCTGCATT TGGGCCTCCCCAT GCTTCTCAGGGAT ACACTCAGCTC (SEQ ID NO: 43) | TAAACTAAAATAT ATCCCTAAAAACA CATAAAAAAACC CAAATACAAAAA CC (SEQ ID NO: 157) | | 16 | R | NM_017869; NM_079837 |
| cg10818160 | DMRTB1 | hypo | GTAGCACTAAGC CTGGCATAGTGTC CTGTGCCTGTAGC CCTAGCTACTCG (SEQ ID NO: 44) | TATAACACTAAAA CCTAACATAATAT CCTATACCTATAA CCCTAACTACTC (SEQ ID NO: 158) | | 1 | F | NM_033067 |

TABLE 2-continued

Illumina ID, related genomic sequences and the level of methylation of the genomic sites in PE patients compared to control

| Illumina ID* | Gene Name | Methyl- ation status in PE Patients | Sequene of the genomic site | AlleleA ProbeSeq** | AlleleB ProbeSeq*** | Ch. No. | Strand Orien- tation**** | UCSC_ RefGene_ Accession |
|---|---|---|---|---|---|---|---|---|
| cg14161477 | TMCO3 | hypo | CGCCGCTCCGCCG TGCTGAGCCCTTG GCGCTGTCATCTG AGTCTTCCGTC (SEQ ID NO: 45) | AACAAAAAACTC AAATAACAAAC CAAAAACTCAAC ACACAAAACAA CA (SEQ ID NO: 158) | AACGAAAAACT CAAATAACAAC GCCAAAAACTC AACACGACGA AACGACG (SEQ ID NO: 189) | 13 | F | NM_017905 |
| cg01916429 | CYP19A1 | hyper | CGAAGCTCATTG AAACAAAGAAAT CCAGAAACATTCT ACTGATCTTTGTG (SEQ ID NO: 46) | CCACAAAATCA ATAAAATATTTCT AAATTCTTTATT TCAATAAACTTC (SEQ ID NO: 159) | | 15 | F | NM_031226; NM_000103 |
| cg01933079 | MAST4 | hyper | AGGGTTTCACAG GGATTTTTCTCAG GAGTGTGCCACA GTGCAAGCTGAC G (SEQ ID NO: 47) | AAAAATTTCACA AAAATTTTTCTCA AAATATACCAC AATACAAACTAA C (SEQ ID NO: 160) | | 5 | F | NM_001164664; NM_198828 |
| cg04224092 | VASH1 | hyper | AAGAGATGGCTC ACCTTGGGAGGT GCCAGGCTGAAA CTAGTCCTTTC G (SEQ ID NO: 48) | AAAAAATAACT CACCTTAAAAA TACCAAACTAA ACTAAATCCTTTC C (SEQ ID NO: 161) | | 14 | R | NM_014909 |
| cg12440187 | GNL1 | hyper | CGGTGGTATGGCT GTAGACAACTGT CTCAGGAAACAG ACCCATGACCCA C (SEQ ID NO: 49) | AATAAATCATAA ATCTATTCCTAA AACAATTATCTAC AACCATACCACC (SEQ ID NO: 162) | | 6 | F | NM_005275 |
| cg14613402 | LHX8 | hyper | ACCACAGGGCTTT TTGCAAGCCCATG GGAAAGACAGCC TGAGAGACTTCG (SEQ ID NO: 50) | AACCACAAAACT TTTTACAAACCCA TAAAAAAACAA CCTAAAAAACTTC (SEQ ID NO: 163) | | 1 | F | NM_001001933 |

TABLE 2-continued

Illumina ID, related genomic sequences and the level of methylation of the genomic sites in PE patients compared to control

| Illumina ID* | Gene Name | Methylation status in PE Patients | Sequence of the genomic site | AlleleA ProbeSeq** | AlleleB ProbeSeq*** | Ch. No. | Strand Orientation**** | UCSC RefGene Accession |
|---|---|---|---|---|---|---|---|---|
| cg15841167 | MOG | hyper | GCAGCTAAGGGA CTTACATCTGAAG TCCCTCAAGGGA CTTTTTATTGACG (SEQ ID NO: 51) | AACAACTAAAAA ACTTACATCTAAA ATCCCTCAAAAA ACTTTTTATTAAC (SEQ ID NO: 165) | | 6 | F | NM_206813; NM_001170418; NM_206814; NM_206811; NM_206810; NM_206809; NM_001170417; NM_001008229; NM_001008228; NM_206812; NM_002433 |
| cg15971010 | SLC47A1 | hyper | CGGACGCCAGGA CTCACCCGGCTC TCCACCTCCGCTG GGGGTTTCAGT (SEQ ID NO: 52) | ACCTAAAACCCC CAACAAAAATAA AAAACCAAAATA AATCCTAACATCC A (SEQ ID NO: 166) | ACCTAAAACCCC CAACGAAAAT AAAAAACCGA AATAAATCCTA ACGTCCG (SEQ ID NO: 190) | 17 | R | NM_018242 |
| cg17428744 | UTP11L | hyper | CGGGTTGCTGTAT CTAGAAGGTATG TTTAAAGCTAGA GCAGTACGGATTT (SEQ ID NO: 53) | TAAATCCRTACTA CTCTAACTTTAAA CATACCTTCTAAA TACACAACCC (SEQ ID NO: 167) | | 1 | R | NM_016037 |
| cg25434223 | ELAVL3 | hyper | CGCCCCCCTAGG AGTGCACCACCC CCGGAGCCCCCT CAACACGGACCG C (SEQ ID NO: 54) | CRCRATCCRTATT AAAAAAACTCC RAAAATAATACA CTCCTAAAAAAA C (SEQ ID NO: 168) | | 19 | R | NM_001420; NM_032281; NM_001420; NM_032281 |
| cg07349464 | PDHX | hyper | TTACCTTCTTTCT TTCTTTCTATTTT TTAGATGAGCCT TACTCTATC (SEQ ID NO: 55) | ATTACCTTCTTTC TTCTTTCTATTTT TTTAATAAAACC TTACTCTATC (SEQ ID NO: 169) | | 11 | R | NM_001135024; NM_001166158; NM_003477 |

*Illumina ID indicates the ID number assigned to the sequence on Infinium HumanMethylation450 v1.2 BeadChip™ (Illumina Inc.).
**Sequence of a probe used to determine the level of methylation in the genomic site associated with the Illumina ID.
***Sequence of a probe used to determine the level of methylation in the genomic site associated with the Illumina ID.
****F indicates forward and R indicates reverse strand sequence.

TABLE 3

Clinical Characteristics of the Study Groups. The characteristics of the women whose samples were used in the study are shown. Categorical data were studied with chi-square analyses. Means and medians of continuous data were studied using parametric and non-parametric tests as indicated. There were no significant between-group differences with respect to any of these characteristics (p-value < 0.05 considered significant). The mean gestational age at delivery was 36.78 ± 2.19 weeks for the cases and 39.86 ± 1.15 weeks for the control group (p < 0.0001). * Plus ± minus values are means ± SD.

| Maternal Characteristic | Cases (n = 16) | Controls (n = 28) |
|---|---|---|
| Maternal age (Years) | 34 ± 5.25 | 32.29 ± 4.42 |
| Race | | |
| White (n, %) | 14 (87.50) | 24 (88.89) |
| Asian (n, %) | 2 (12.50) | 3 (11.11) |
| Parity | 0.25 ± 0.45 | 0.32 ± 0.48 |
| BMI | 23.75 ± 4.28 | 22.43 ± 3.32 |
| Gestational age at enrollment (weeks) | 12.69 ± 0.71 | 12.47 ± 0.54 |

TABLE 4

Relevance of the significantly altered microRNAs to PE. Detail descriptions of 22 significant microRNAs are shown.

| miRNA | Cluster Members | Pathways [Targets related to PE mechanisms] | Associated disorders | Epigenetic Targets | PMID related to PE |
|---|---|---|---|---|---|
| let-7a-5p | let-7a, let-7c | PI3K/AKT, PTEN, HGF, IL-8. [CCND, IGF2, (ADAMTS1,−14, −15, −5, −8), IGF2BP1-3, PAPPA] | Reproductive Disorders, Connective Tissue Disorders, Cancer | EZH2, UHRF1 | 21840305 (3rd trimester PE plasma) |
| miR-126a-3p | miR-126 | PPARa/RXRa Activation, Angiogenesis, Inflammation, Cardiac Hypertrophy [IRS1, ADAM9, VEGFA] | Reproductive Disorders, Connective Tissue Disorders, Cancer | — | 23553946 (PE placenta at term, EPC from placenta), 24811064 (1st trimester pooled samples) |
| miR-128-3p | miR-128a | Epithelial Neoplasia, Mammary Neoplasm, Angiogenesis [VEGF, TGFBR1, WEE1, glucocorticoid, SERPINE1] | Cervical Cancer, Glioblastoma Cancer, Myelodysplastic Syndrome with 5q-syndrome | HDAC4, HDAC5, KMT2A, MBD1, SIRT1 | 21309633 (PE placenta) |
| miR-130a-3p | miR-130b | Endometriosis, Epithelial neoplasia, Breast Cancer [COL1A1, HOXB7, SERPINE1] | Severe PE, Cancer | KMT2A, MBD4 | 22187671 (PE plasma 37-40 weeks) |
| miR-140-3p | miR-140-3p | Hematological Neoplasia, Cell Lymphoma, Breast Cancer [IGFBP1, HDAC4] | Cancer | HDAC4, HDAC5, MBD1, SIRT1, SIRT3 | n/a |
| miR-142-3p | miR-142-3p | VEGF, Apoptosis, PI3K/AKT, PTEN, IL-8, Inflammation [BCL2L1] | Reproductive Disorders (fetal neural tube defect), Connective Tissue Disorders, Cancer | — | n/a |
| miR-146a-5p | miR-146b | IL-6 signaling, IL-10 signaling, PPAR signaling [RUNX1T1, INHBA, IL8] | Cell Death and Survival, Inflammatory response, Preeclampsia | UHRF1 | n/a |
| miR-16-5p | miR-15a | TGF-β, STAT3 signaling, Angiogenesis, Inflammation [WNT3A, VEGF, IGF2] | Severe Late-onset PE, Reproductive Disorders, Connective Tissue Disorders, Cancer. | KMT2A, MBD1, SIRT4 | 19642860 (placenta), 22251611 (studied in plasma 12-16 weeks but no diff in PE), 23083510 (mesenchymal stem cells) |
| miR-17-5p | miR-17, miR-106a, miR-20a | Angiogenesis, NFAT Cardiac Hypertrophy, Glioblastoma Multiforme [VEGFA, RB1, TGFBR2, ADAM9, ADAMTS5] | PE, Reproductive Disorders, Connective Tissue Disorders, Cancer | HDAC4, HDAC5, KMT2A, SIRT7 | 23438603 (PE placenta), 22438230 (PE placenta) |
| miR-191-5p | miR-191 | IL-6 signaling, Glucocorticoid receptor signaling [IL6, HLTF, CEBPB] | Inflammatory response, Reproductive system disease | — | 23830491 (PE placenta) |
| miR-196a-5p | miR-196b | Endothelial dysfunction, STAT3, PTEN signaling [IGF1, CDC25A, TGFBR3] | Cell Death and Survival, Cardiovascular System Development and Function | — | n/a |

TABLE 4-continued

Relevance of the significantly altered microRNAs to PE.
Detail descriptions of 22 significant microRNAs are shown.

| miRNA | Cluster Members | Pathways [Targets related to PE mechanisms] | Associated disorders | Epigenetic Targets | PMID related to PE |
|---|---|---|---|---|---|
| miR-19b-3p | miR-19b | Hypoxia, Endothelial Dysfunction, Oxidative Stress [LIF, IGF1, LDLR] | Cell Death and Survival, Inflammatory Disease, Preterm Birth, PE | HDAC4, MBD4, PCGF2, SIRT5 | 23438603 (PE placenta) |
| miR-26a-5p | miR-26a | TGF-β, NGF signaling, Endothelial dysfunction [IGF1, INHBB, SMAD4] | Late onset PE, Premature labor, Cellular movement | DNMT3B, EZH2 | 23830491 (PE placenta), 22187671 (PE plasma 37-40 weeks) |
| miR-296-5p | miR-296 | Preeclampsia and Preterm Labor [ADAM17] | PE, Reproductive Disorders | DNMT3B, HDAC5, EHMT1, KMT2A, MBD4, PCGF2, SIRT5 | 23830491 (PE placenta), 19285651 (PE placenta) |
| miR-29b-3p | miR-29a | Angiogenesis, Systemic Inflammatory response, Hypoxia [VEGFA, STAT3, LIF] | Late onset PE, Disorder of Pregnancy, Cardiovascular System Development and Function | DNMT3A, DNMT3B, HDAC4, SIRT1 | 22716646 (PE placenta), 19642860 (PE placenta) |
| miR-331-5p | miR-331-5p | Apoptosis, PI3K, Leukocyte extravasation signaling [KRAS, LYN, CDH5] | Cell Death and Survival, Inflammatory response, Cellular Movement | — | n/a |
| miR-517a-3p | miR-517a | Hypopharyngeal Squamous Cell Carcinoma, Epithelial Neoplasia [IGF1, IL1A] | PE, IUGR. | — | 22251611 (plasma 12-16 weeks), 24347821 (PE plasma) |

TABLE 5

Canonical pathways, diseases and functions associated with hypermethylated and hypomethylated genes. IPA was carried out to analyze the involvement of methylated genes in several canonical pathways and disease and function. Pathways and the disease functions associated with the methylated genes are directly or indirectly related to PE.

| HYPERMETHYLATED GENES | HYPOMETHYLATED GENES |
|---|---|
| Top Canonical Pathways | Top Canonical Pathways |
| FXR/RXR Activation | Guanine and Guanosine Salvage I |
| Bupropion Degradation | Adenine and Adenosine Salvage III |
| Acetone Degradation I (to Methylglyoxal) | OX40 Signaling Pathway |
| Estrogen Biosynthesis | Sphingomyelin Metabolism |
| Nicotine Degradation III | TREM1 Signaling |
| Associated network Diseases and Functions | Associated network Diseases and Functions |
| Immunological Disease, Inflammatory Disease, Inflammatory Response | Tissue Development, Cardiovascular System Development and Function, Organismal Development |
| Lipid Metabolism, Small Molecule Biochemistry, Vitamin and Mineral Metabolism | Cancer, Cellular Development, Cellular Growth and Proliferation |
| Gene Expression, Cellular Development, Endocrine System Development and Function | Cell-To-Cell Signaling and Interaction, Cellular Function and Maintenance, Cellular Development |
| | Cell Signaling, Molecular Transport, Vitamin and Mineral Metabolism |
| | Cellular Development, Tissue Development, Cellular Growth and Proliferation |

REFERENCES

1. Eads C, Laird P. Combined bisulfite restriction analysis (COBRA). Methods Mol Biol. 2002; 200:71-85.
2. Xiong Z, Laird P. COBRA: a sensitive and quantitative DNA methylation assay. Nucleic Acids Res. 1997; 25:2532-4.
3. Paul C, Clark S. Cytosine methylation: quantitation by automated genomic sequencing and GENESCAN analysis. Biotechniques. 1996; 21:126-33.
4. Warnecke P, Stirzaker C, Song J, Grunau C, Melki J, Clark S. Identification and resolution of artifacts in bisulfite sequencing. Methods. 2002; 27:101-7.
5. Tost J, Gut I. Analysis of gene-specific DNA methylation patterns by pyrosequencing technology. Methods Mol Biol. 2007; 373:89-102.
6. Ehrich M, Nelson M, Stanssens P, Zabeau M, Liloglou T, Xinarianos G, et al. Quantitative high-throughput analysis of DNA methylation patterns by base-specific cleavage and mass spectrometry. Proc Natl Acad Sci USA. 2005; 102:15785-90.
7. Harvey D J, Proteomic analysis of glycosylation: structural determination of N- and O-linked glycans by mass spectrometry. Expert Review of Proteomics 2005, 2(1): 87-101.
8. Su, X., et al. Liquid chromatography mass spectrometry profiling of histones. Journal of Chromatography. B, Analytical technologies in the biomedical and life sciences 2007; 850, 440-454.
9. Wang S, Aurora A B, Johnson B A, Qi X, McAnally J, Hill J A, Richardson J A, Bassel-Duby R, Olson E N. The endothelial-specific microRNA miR-126 governs vascular integrity and angiogenesis. Dev Cell. 2008; 15:261-271.
10. Hong, F., Li, Y., and Xu, Y. (2014) Decreased placental miR-126 expression and vascular endothelial growth factor levels in patients with pre-eclampsia. J. Int. Med. Res. 42, 1243-1251.

---

I claim:

1. A method of predicting the development of preeclampsia (PE) in a subject, the method comprising:
   (a) determining the levels of one or more biomarkers from each of the following four biomarker types: miRNAs, wherein the miRNA is miR-7a, miR-7c, miR-93, mir-106a, mir-126, miR-128a, miR-130b, miR-140-3p, miR-142-3p, miR-146b, miR-15a-5p, miR-17, miR-191, miR-196, miR-19b-1, miR-20a, miR-331-5p, miR-886-5p, miR-26a, miR-29a, miR-517a and miR-296; post-translational modification of H4 histone protein; an amount of HDAC5 mRNA and/or protein; and methylation of CYP19A1 in:
      i) a test sample obtained from the subject in the first trimester of pregnancy, and
      ii) optionally a control sample;
   (b) optionally obtaining one or more reference values corresponding to levels of one or more biomarkers, wherein the presence of four or more biomarkers:
   at different levels in the test sample as compared to the control sample, or
   relative to the reference values indicates high risk of development of PE in the subject;
   (c) identifying the subject as having high risk of developing PE based on the levels of the four or more biomarkers in the test sample; and
   (d) administering a therapy to the subject to treat and/or manage PE to the subject identified as having a high risk of developing PE.

2. The method of claim 1, wherein the subject is identified as having high risk of the development of PE if all of the analyzed biomarkers are significantly different between the test sample and the control sample.

3. The method of claim 1, wherein the subject is identified as having high risk of the development of PE if a predetermined number of biomarkers out of the analyzed biomarkers are significantly different between the test sample and the control sample.

4. The method of claim 1, wherein the subject is identified as having high risk of the development of PE if the four or more biomarkers as a combination are significantly different between the test sample and the control sample.

5. The method of claim 1, wherein the four or more biomarkers comprise miR-17, post-translational modification of H4 histone protein, amount of HDAC5 mRNA and/or protein and methylation of CYP19A1, and the subject is identified as having a high risk of the development of PE if the subject has increased miR-17, hyperacetylated H4 histone protein, hypermethylated CYP19A1, and decreased HDAC5 mRNA and/or protein levels.

6. The method of claim 1, wherein the four or more biomarkers comprise miR-17, post-translational modification of H4 histone protein, methylation of CYP19A1, and the amount of HDAC5 mRNA and/or protein.

7. The method of claim 1, wherein the therapy administered to the subject to manage PE is selected from:
   i) administering medications to lower blood pressure,
   ii) administering corticosteroids, iii) administering anticonvulsant medications,
iv) bed rest for the subject,
v) performing regular non-stress tests or biophysical profiles to monitor the fetus' well-being and measure the volume of amniotic fluid,
vi) administering low-dose aspirin,
vii) administering calcium supplements, and/or
viii) inducing delivery before natural labor is initiated.

\* \* \* \* \*

SEQUENCE LISTING

```
<160> NUMBER OF SEQ ID NOS: 191

<210> SEQ ID NO 1
<211> LENGTH: 102
<212> TYPE: PRT
<213> ORGANISM: Homo sapiens

<400> SEQUENCE: 1

Ser Gly Arg Gly Lys Gly Gly Lys Gly Leu Gly Lys Gly Ala Lys
1               5                   10                  15

Arg His Arg Lys Val Leu Arg Asp Asn Ile Gln Gly Ile Thr Lys Pro
                20                  25                  30

Ala Ile Arg Arg Leu Ala Arg Arg Gly Gly Val Lys Arg Ile Ser Gly
            35                  40                  45

Leu Ile Tyr Glu Glu Thr Arg Gly Val Leu Lys Val Phe Leu Glu Asn
        50                  55                  60

Val Ile Arg Asp Ala Val Thr Tyr Thr Glu His Ala Lys Arg Lys Thr
65                  70                  75                  80

Val Thr Ala Met Asp Val Val Tyr Ala Leu Lys Arg Gln Gly Arg Thr
                85                  90                  95

Leu Tyr Gly Phe Gly Gly
            100

<210> SEQ ID NO 2
<211> LENGTH: 50
<212> TYPE: DNA
<213> ORGANISM: Homo sapiens

<400> SEQUENCE: 2
cggtactcac agctggacac aaacatagct tgcaggagga agagtgtcag          50

<210> SEQ ID NO 3
<211> LENGTH: 50
<212> TYPE: DNA
<213> ORGANISM: Homo sapiens

<400> SEQUENCE: 3
cgtccgccag ggaagctgtc agggattatc tgcggttcct gagtagctga          50

<210> SEQ ID NO 4
<211> LENGTH: 50
```

```
<212> TYPE: DNA
<213> ORGANISM: Homo sapiens

<400> SEQUENCE: 4
ttagttttgg atcctcaact tctggaacag cgcagggcac acagtagacg              50

<210> SEQ ID NO 5
<211> LENGTH: 50
<212> TYPE: DNA
<213> ORGANISM: Homo sapiens

<400> SEQUENCE: 5
gttactcttc cagggtgcac acaagaggca atgaagccca gggaattacg              50

<210> SEQ ID NO 6
<211> LENGTH: 50
<212> TYPE: DNA
<213> ORGANISM: Homo sapiens

<400> SEQUENCE: 6
cgctgaagcc ccattccaga ccctgcttct gacaaacctg aactaaggca              50

<210> SEQ ID NO 7
<211> LENGTH: 50
<212> TYPE: DNA
<213> ORGANISM: Homo sapiens

<400> SEQUENCE: 7
cgagatggga agattatcct gaccctaaat acacaagtgt cctaagagga              50

<210> SEQ ID NO 8
<211> LENGTH: 50
<212> TYPE: DNA
<213> ORGANISM: Homo sapiens

<400> SEQUENCE: 8
cggccgcggc tctgatgctt ttgcaggcgg cattgtgtca ctgattcact              50

<210> SEQ ID NO 9
<211> LENGTH: 50
<212> TYPE: DNA
<213> ORGANISM: Homo sapiens

<400> SEQUENCE: 9
cgctggctct gcttccattc ctgaagtctc aggctctccc agggtgtcag              50

<210> SEQ ID NO 10
<211> LENGTH: 50
<212> TYPE: DNA
<213> ORGANISM: Homo sapiens

<400> SEQUENCE: 10
cggcccccgc agccgtcacg gctgctgcag ctgttgcgac ccctcccacc              50

<210> SEQ ID NO 11
<211> LENGTH: 50
<212> TYPE: DNA
<213> ORGANISM: Homo sapiens

<400> SEQUENCE: 11
cagtgccaaa aaatatcagg tggtgttcat caaaaaagct gagccaaccg              50

<210> SEQ ID NO 12
```

```
<211> LENGTH: 50
<212> TYPE: DNA
<213> ORGANISM: Homo sapiens

<400> SEQUENCE: 12 cgcccccat cctgagcctg caggggccgc cagctggtcc aatcccccca            50

<210> SEQ ID NO 13
<211> LENGTH: 50
<212> TYPE: DNA
<213> ORGANISM: Homo sapiens

<400> SEQUENCE: 13
ttgtctccag ctagagggc gcggagcggc cagagagcta gagggcagcg            50

<210> SEQ ID NO 14
<211> LENGTH: 50
<212> TYPE: DNA
<213> ORGANISM: Homo sapiens

<400> SEQUENCE: 14
gaactgccac aaagtcatag cttctttttt tttcttgaga tagggtctcg            50

<210> SEQ ID NO 15
<211> LENGTH: 50
<212> TYPE: DNA
<213> ORGANISM: Homo sapiens

<400> SEQUENCE: 15
gtggagtcac ccggccacac tcggtgggg cccaggaatg acgggggcg              50

<210> SEQ ID NO 16
<211> LENGTH: 50
<212> TYPE: DNA
<213> ORGANISM: Homo sapiens

<400> SEQUENCE: 16
atctcatggt tcaccgttttt ttaagcccgt cggaaaagcg cagtattccg           50

<210> SEQ ID NO 17
<211> LENGTH: 50
<212> TYPE: DNA
<213> ORGANISM: Homo sapiens

<400> SEQUENCE: 17
cgaggaaact gaggcttaga tcagctatac cacttgttca agtctacaaa            50

<210> SEQ ID NO 18
<211> LENGTH: 50
<212> TYPE: DNA
<213> ORGANISM: Homo sapiens

<400> SEQUENCE: 18
cggtcccatc cctccagcgt cccgctcagc tccagcagcc aggagcccgc            50

<210> SEQ ID NO 19
<211> LENGTH: 50
<212> TYPE: DNA
<213> ORGANISM: Homo sapiens

<400> SEQUENCE: 19
cgccccgccc gctcacaggt ctccgcgcag cctcgctcac ctgtgtccgc            50
```

<210> SEQ ID NO 20
<211> LENGTH: 50
<212> TYPE: DNA
<213> ORGANISM: Homo sapiens

<400> SEQUENCE: 20
cctcataggc atctgggctg tgacgcttag gattcctaaa tagtctctcg    50

<210> SEQ ID NO 21
<211> LENGTH: 50
<212> TYPE: DNA
<213> ORGANISM: Homo sapiens

<400> SEQUENCE: 21
cgcttagtgt cctgagcatc tgtgggaagc tgacacagcc tcactcctgc    50

<210> SEQ ID NO 22
<211> LENGTH: 50
<212> TYPE: DNA
<213> ORGANISM: Homo sapiens

<400> SEQUENCE: 22
tgttacagtt ctcattggga ggtttctctt tgagcatgaa cttggtagcg    50

<210> SEQ ID NO 23
<211> LENGTH: 50
<212> TYPE: DNA
<213> ORGANISM: Homo sapiens

<400> SEQUENCE: 23
cggctcactg caagctccgc ctcgggaaaa catgggggtg gttccacctc    50

<210> SEQ ID NO 24
<211> LENGTH: 50
<212> TYPE: DNA
<213> ORGANISM: Homo sapiens

<400> SEQUENCE: 24
gggggcccgg ctgatgggga cccggctgat ggggggccgg aagacaacg    50

<210> SEQ ID NO 25
<211> LENGTH: 50
<212> TYPE: DNA
<213> ORGANISM: Homo sapiens

<400> SEQUENCE: 25
cgccgcgacc tgcgaccctc aagaccccca ccccgccaa gccccgcccc    50

<210> SEQ ID NO 26
<211> LENGTH: 50
<212> TYPE: DNA
<213> ORGANISM: Homo sapiens

<400> SEQUENCE: 26
cgccatttta tatatgggac ttgagcatcc tgcattttgg taactgcgag    50

<210> SEQ ID NO 27
<211> LENGTH: 50
<212> TYPE: DNA
<213> ORGANISM: Homo sapiens

<400> SEQUENCE: 27
cgggacctgc agcctgacat gcccgagccc caccctgcc actcccgtga    50

<210> SEQ ID NO 28
<211> LENGTH: 50
<212> TYPE: DNA
<213> ORGANISM: Homo sapiens

<400> SEQUENCE: 28
cgctactgca gcataaatta gctcatcctg actgataaca aaagggatat                50

<210> SEQ ID NO 29
<211> LENGTH: 50
<212> TYPE: DNA
<213> ORGANISM: Homo sapiens

<400> SEQUENCE: 29
cgcactcggc ctgacccacg gcgaccctct gtgaccaatc atactaccaa                50

<210> SEQ ID NO 30
<211> LENGTH: 50
<212> TYPE: DNA
<213> ORGANISM: Homo sapiens

<400> SEQUENCE: 30
aacccattat caacgtcatt aggatccaag tttcggctca caagggaccg                50

<210> SEQ ID NO 31
<211> LENGTH: 50
<212> TYPE: DNA
<213> ORGANISM: Homo sapiens

<400> SEQUENCE: 31
cggccagttc cttctggaca ccttgtctgt ccttgagcta tcatgtaatc                50

<210> SEQ ID NO 32
<211> LENGTH: 50
<212> TYPE: DNA
<213> ORGANISM: Homo sapiens

<400> SEQUENCE: 32
tcctgtagta attggggaaa catgccaaat tttccttttg ccctttttgcg               50

<210> SEQ ID NO 33
<211> LENGTH: 50
<212> TYPE: DNA
<213> ORGANISM: Homo sapiens

<400> SEQUENCE: 33
cgccgcacct ccacttctgc ccatgcttgt cctgtgaccc tcgtggtcat                50

<210> SEQ ID NO 34
<211> LENGTH: 50
<212> TYPE: DNA
<213> ORGANISM: Homo sapiens

<400> SEQUENCE: 34
tccacctaca ccaatggttt atggagcagc caagagtttg tgaggaggcg                50

<210> SEQ ID NO 35
<211> LENGTH: 50
<212> TYPE: DNA
<213> ORGANISM: Homo sapiens

<400> SEQUENCE: 35
cggggctgtc tctcactggc aggggccacc tctccgtgga ccgacctgag                50

<210> SEQ ID NO 36
<211> LENGTH: 50
<212> TYPE: DNA
<213> ORGANISM: Homo sapiens

<400> SEQUENCE: 36
gacgcggggg ctgcaagaac acggggagac gtgtgcccct tgggttcccg                50

<210> SEQ ID NO 37
<211> LENGTH: 50
<212> TYPE: DNA
<213> ORGANISM: Homo sapiens

<400> SEQUENCE: 37
cggctcctgc caccccgac tcccccatct ggagacagtg gtgggggag                50

<210> SEQ ID NO 38
<211> LENGTH: 50
<212> TYPE: DNA
<213> ORGANISM: Homo sapiens

<400> SEQUENCE: 38
gccagaagtc caccccaggg cctctgcggc cctggagagg caggatggcg                50

<210> SEQ ID NO 39
<211> LENGTH: 50
<212> TYPE: DNA
<213> ORGANISM: Homo sapiens

<400> SEQUENCE: 39
tattgcttct gcaccaatat aaagttaaaa aattctaaga caagccatcg                50

<210> SEQ ID NO 40
<211> LENGTH: 50
<212> TYPE: DNA
<213> ORGANISM: Homo sapiens

<400> SEQUENCE: 40
aggacggagc agcaacgtgg gccagggcag gggtgcagga aagcaacgcg                50

<210> SEQ ID NO 41
<211> LENGTH: 50
<212> TYPE: DNA
<213> ORGANISM: Homo sapiens

<400> SEQUENCE: 41
tcttgaagca tcaccccacc tggggagggt ttggagcatg aagtgggccg                50

<210> SEQ ID NO 42
<211> LENGTH: 50
<212> TYPE: DNA
<213> ORGANISM: Homo sapiens

<400> SEQUENCE: 42
tcagtgggcc cttccttcgg gcggacccca gagtcaccgc agagtggtcg                50

<210> SEQ ID NO 43
<211> LENGTH: 50
<212> TYPE: DNA
<213> ORGANISM: Homo sapiens

<400> SEQUENCE: 43
cggcccctgc atttgggcct ccccatgctt ctcagggata cactcagctc        50

<210> SEQ ID NO 44
<211> LENGTH: 50
<212> TYPE: DNA
<213> ORGANISM: Homo sapiens

<400> SEQUENCE: 44
gtagcactaa gcctggcata gtgtcctgtg cctgtagccc tagctactcg        50

<210> SEQ ID NO 45
<211> LENGTH: 50
<212> TYPE: DNA
<213> ORGANISM: Homo sapiens

<400> SEQUENCE: 45
cgccgctccg ccgtgctgag cccttggcgc tgtcatctga gtcttccgtc        50

<210> SEQ ID NO 46
<211> LENGTH: 50
<212> TYPE: DNA
<213> ORGANISM: Homo sapiens

<400> SEQUENCE: 46
cgaagctcat tgaaacaaag aaatccagaa acattctact gatctttgtg        50

<210> SEQ ID NO 47
<211> LENGTH: 50
<212> TYPE: DNA
<213> ORGANISM: Homo sapiens

<400> SEQUENCE: 47
agggtttcac agggattttt ctcaggagtg tgccacagtg caagctgacg        50

<210> SEQ ID NO 48
<211> LENGTH: 50
<212> TYPE: DNA
<213> ORGANISM: Homo sapiens

<400> SEQUENCE: 48
aagagatggc tcaccttggg aggtgccagg ctgaaactag gtccttttccg       50

<210> SEQ ID NO 49
<211> LENGTH: 50
<212> TYPE: DNA
<213> ORGANISM: Homo sapiens

<400> SEQUENCE: 49
cggtggtatg gctgtagaca actgtctcag gaaacagacc catgacccac        50

<210> SEQ ID NO 50
<211> LENGTH: 50
<212> TYPE: DNA
<213> ORGANISM: Homo sapiens

<400> SEQUENCE: 50
accacagggc ttttgcaag cccatgggaa agacagcctg agagacttcg         50

<210> SEQ ID NO 51
<211> LENGTH: 50
<212> TYPE: DNA
<213> ORGANISM: Homo sapiens

<400> SEQUENCE: 51

```
gcagctaagg gacttacatc tgaagtccct caagggactt tttattgacg            50

<210> SEQ ID NO 52
<211> LENGTH: 50
<212> TYPE: DNA
<213> ORGANISM: Homo sapiens

<400> SEQUENCE: 52
cggacgccag gactcacccc ggctctccac ctccgctggg ggtttcaggt            50

<210> SEQ ID NO 53
<211> LENGTH: 50
<212> TYPE: DNA
<213> ORGANISM: Homo sapiens

<400> SEQUENCE: 53
cgggttgctg tatctagaag gtatgtttaa agctagagca gtacggattt            50

<210> SEQ ID NO 54
<211> LENGTH: 50
<212> TYPE: DNA
<213> ORGANISM: Homo sapiens

<400> SEQUENCE: 54
cgccccccta ggagtgcacc accccggag ccccccctcaa cacggaccgc             50

<210> SEQ ID NO 55
<211> LENGTH: 50
<212> TYPE: DNA
<213> ORGANISM: Homo sapiens

<400> SEQUENCE: 55
ttaccttctt tctttctttc tatttttta gatggagcct tactctgtcg             50

<210> SEQ ID NO 56
<211> LENGTH: 84
<212> TYPE: DNA
<213> ORGANISM: Homo sapiens

<400> SEQUENCE: 56
gcauccgggu ugagguagua ggцuguaugg uuuagaguua cacccuggga guuaacugua  60
caaccuucua gcuuuccuug gagc                                        84

<210> SEQ ID NO 57
<211> LENGTH: 22
<212> TYPE: DNA
<213> ORGANISM: Homo sapiens

<400> SEQUENCE: 57
ugagguagua ggцuguaugg uu                                          22

<210> SEQ ID NO 58
<211> LENGTH: 80
<212> TYPE: DNA
<213> ORGANISM: Homo sapiens

<400> SEQUENCE: 58 cuggggcuc caaagugcug uucgugcagg uagugugauu acccaaccua cugcugagcu   60
agcacuuccc gagcccccgg                                             80

<210> SEQ ID NO 59
```

```
<211> LENGTH: 23
<212> TYPE: DNA
<213> ORGANISM: Homo sapiens

<400> SEQUENCE: 59
caaagugcug uucgugcagg uag                                              23

<210> SEQ ID NO 60
<211> LENGTH: 82
<212> TYPE: DNA
<213> ORGANISM: Homo sapiens

<400> SEQUENCE: 60
ugagcuguug gauucggggc cguagcacug ucugagaggu uuacauuucu cacagugaac      60
cggucucuuu uucagcugcu uc                                               82

<210> SEQ ID NO 61
<211> LENGTH: 23
<212> TYPE: DNA
<213> ORGANISM: Homo sapiens

<400> SEQUENCE: 61
cggggccgua gcacugucug aga                                              23

<210> SEQ ID NO 62
<211> LENGTH: 100
<212> TYPE: DNA
<213> ORGANISM: Homo sapiens

<400> SEQUENCE: 62
ugugucucuc ucugugaccu gccagugguu uuacccuaug guagguuacg ucaugcuguu      60
cuaccacagg guagaaccac ggacaggaua ccggggcacc                           100

<210> SEQ ID NO 63
<211> LENGTH: 21
<212> TYPE: DNA
<213> ORGANISM: Homo sapiens

<400> SEQUENCE: 63
uaccacaggg uagaaccacg g                                                21

<210> SEQ ID NO 64
<211> LENGTH: 87
<212> TYPE: DNA
<213> ORGANISM: Homo sapiens

<400> SEQUENCE: 64
gacagugcag ucacccauaa aguagaaagc acuacuaaca gcacuggagg guguaguguu      60
uccuacuuua uggaugagug uacgugg                                          87

<210> SEQ ID NO 65
<211> LENGTH: 23
<212> TYPE: DNA
<213> ORGANISM: Homo sapiens

<400> SEQUENCE: 65
uguaguguuu ccuacuuuau gga                                              23

<210> SEQ ID NO 66
<211> LENGTH: 73
<212> TYPE: DNA
<213> ORGANISM: Homo sapiens
```

<400> SEQUENCE: 66
ccuggcacug agaacugaau uccauaggcu gugagcucua gcaaugcccu guggacucag    60
uucuggugcc cgg    73

<210> SEQ ID NO 67
<211> LENGTH: 22
<212> TYPE: DNA
<213> ORGANISM: Homo sapiens

<400> SEQUENCE: 67
ugagaacuga auuccauagg cu    22

<210> SEQ ID NO 68
<211> LENGTH: 83
<212> TYPE: DNA
<213> ORGANISM: Homo sapiens

<400> SEQUENCE: 68
ccuuggagua aaguagcagc acauaauggu uuguggauuu ugaaaaggug caggccauau    60
ugugcugccu caaaaauaca agg    83

<210> SEQ ID NO 69
<211> LENGTH: 22
<212> TYPE: DNA
<213> ORGANISM: Homo sapiens

<400> SEQUENCE: 69
uagcagcaca uaaugguuug ug    22

<210> SEQ ID NO 70
<211> LENGTH: 84
<212> TYPE: DNA
<213> ORGANISM: Homo sapiens

<400> SEQUENCE: 70
acuggucggu gauuuaggua guuuccuguu guugggaucc accuuucucu cgacagcacg    60
acacugccuu cauuacuuca guug    84

<210> SEQ ID NO 71
<211> LENGTH: 22
<212> TYPE: DNA
<213> ORGANISM: Homo sapiens

<400> SEQUENCE: 71
uagguaguuu ccuguuguug gg    22

<210> SEQ ID NO 72
<211> LENGTH: 94
<212> TYPE: DNA
<213> ORGANISM: Homo sapiens

<400> SEQUENCE: 72
gaguuugguu uuguuggguu uuguucuagg uaugguccca gggaucccag aucaaaccag    60
gccccugggc cuauccuaga accaaccuaa gcuc    94

<210> SEQ ID NO 73
<211> LENGTH: 22
<212> TYPE: DNA
<213> ORGANISM: Homo sapiens

```
<400> SEQUENCE: 73
cuagguaugg ucccagggau cc                                            22

<210> SEQ ID NO 74
<211> LENGTH: 121
<212> TYPE: DNA
<213> ORGANISM: Homo sapiens

<400> SEQUENCE: 74
cacuccuacc cggducggag uuagcucaag cgguuaccuc cucaugccgg acuuucuauc    60
uguccaucuc ugugcugggg uucgagaccc gcgggugcuu acugacccuu uuaugcaaua   120
a                                                                  121

<210> SEQ ID NO 75
<211> LENGTH: 23
<212> TYPE: DNA
<213> ORGANISM: Homo sapiens

<400> SEQUENCE: 75
cgggucggag uuagcucaag cgg                                           23

<210> SEQ ID NO 76
<211> LENGTH: 84
<212> TYPE: DNA
<213> ORGANISM: Homo sapiens

<400> SEQUENCE: 76
gucagaauaa ugucaaagug cuuacagugc agguagugau augugcaucu acugcaguga   60
aggcacuugu agcauuaugg ugac                                          84

<210> SEQ ID NO 77
<211> LENGTH: 23
<212> TYPE: DNA
<213> ORGANISM: Homo sapiens

<400> SEQUENCE: 77
caaagugcuu acagugcagg uag                                           23

<210> SEQ ID NO 78
<211> LENGTH: 77
<212> TYPE: DNA
<213> ORGANISM: Homo sapiens

<400> SEQUENCE: 78
guggccucgu ucaaguaauc caggauaggc ugugcagguc ccaaugggcc uauucuuggu   60
uacuugcacg gggacgc                                                  77

<210> SEQ ID NO 79
<211> LENGTH: 22
<212> TYPE: DNA
<213> ORGANISM: Homo sapiens

<400> SEQUENCE: 79
uucaaguaau ccaggauagg cu                                            22

<210> SEQ ID NO 80
<211> LENGTH: 77
<212> TYPE: DNA
<213> ORGANISM: Homo sapiens

<400> SEQUENCE: 80
```

```
guggccucgu ucaaguaauc caggauaggc ugugcagguc ccaaugggcc uauucuuggu    60
uacuugcacg gggacgc                                                  77

<210> SEQ ID NO 81
<211> LENGTH: 22
<212> TYPE: DNA
<213> ORGANISM: Homo sapiens

<400> SEQUENCE: 81
ccuauucuug guuacuugca cg                                            22

<210> SEQ ID NO 82
<211> LENGTH: 82
<212> TYPE: DNA
<213> ORGANISM: Homo sapiens

<400> SEQUENCE: 82
ggccugcccg acacucuuuc ccuguugcac uacauaggc cgcugggaag cagugcaaug    60
augaaagggc aucggucagg uc                                            82

<210> SEQ ID NO 83
<211> LENGTH: 21
<212> TYPE: DNA
<213> ORGANISM: Homo sapiens

<400> SEQUENCE: 83
acucuuuccc uguugcacua c                                             21

<210> SEQ ID NO 84
<211> LENGTH: 72
<212> TYPE: DNA
<213> ORGANISM: Homo sapiens

<400> SEQUENCE: 84
agguugaggu aguagguugu auaguuuaga auuacaucaa gggagauaac uguacagccu    60
ccuagcuuuc cu                                                       72

<210> SEQ ID NO 85
<211> LENGTH: 22
<212> TYPE: DNA
<213> ORGANISM: Homo sapiens

<400> SEQUENCE: 85
ugagguagua gguuguauag uu                                            22

<210> SEQ ID NO 86
<211> LENGTH: 64
<212> TYPE: DNA
<213> ORGANISM: Homo sapiens

<400> SEQUENCE: 86
augacugauu ucuuuuggug uucagaguca auauaauuuu cuagcaccau cugaaaucgg    60
uuau                                                                64

<210> SEQ ID NO 87
<211> LENGTH: 22
<212> TYPE: DNA
<213> ORGANISM: Homo sapiens

<400> SEQUENCE: 87
```

-continued

| acugauuucu uuuggguguuc ag | 22 |

<210> SEQ ID NO 88
<211> LENGTH: 87
<212> TYPE: DNA
<213> ORGANISM: Homo sapiens

<400> SEQUENCE: 88

| ucucaggcag ugacccucua gauggaagca cugucuguug uauaaaagaa aagaucgugc | 60 |
| aucccuuuag aguguuacug uuugaga | 87 |

<210> SEQ ID NO 89
<211> LENGTH: 22
<212> TYPE: DNA
<213> ORGANISM: Homo sapiens

<400> SEQUENCE: 89

| ccucuagaug gaagcacugu cu | 22 |

<210> SEQ ID NO 90
<211> LENGTH: 92
<212> TYPE: DNA
<213> ORGANISM: Homo sapiens

<400> SEQUENCE: 90

| cggcuggaca gcgggcaacg gaaucccaaa agcagcuguu gucccagag cauuccagcu | 60 |
| gcgcuuggau uucgucccu gcucuccugc cu | 92 |

<210> SEQ ID NO 91
<211> LENGTH: 23
<212> TYPE: DNA
<213> ORGANISM: Homo sapiens

<400> SEQUENCE: 91

| caacggaauc ccaaaagcag cug | 23 |

<210> SEQ ID NO 92
<211> LENGTH: 80
<212> TYPE: DNA
<213> ORGANISM: Homo sapiens

<400> SEQUENCE: 92

| aggacccuuc cagagggccc ccccucaauc cuguugugcc uaauucagag gguugggugg | 60 |
| aggcucuccu gaagggcucu | 80 |

<210> SEQ ID NO 93
<211> LENGTH: 21
<212> TYPE: DNA
<213> ORGANISM: Homo sapiens

<400> SEQUENCE: 93

| agggcccccc cucaauccug u | 21 |

<210> SEQ ID NO 94
<211> LENGTH: 71
<212> TYPE: DNA
<213> ORGANISM: Homo sapiens

<400> SEQUENCE: 94

| uguucuaagg ugcaucuagu gcagauagug aaguagauua gcaucuacug cccuaagugc | 60 |
| uccuucuggc a | 71 |

<210> SEQ ID NO 95
<211> LENGTH: 23
<212> TYPE: DNA
<213> ORGANISM: Homo sapiens

<400> SEQUENCE: 95
uaaggugcau cuagugcaga uag                                          23

<210> SEQ ID NO 96
<211> LENGTH: 82
<212> TYPE: DNA
<213> ORGANISM: Homo sapiens

<400> SEQUENCE: 96 gcagccucu guuaguuuug cauaguugca cuacaagaag aauguaguug ugcaaaucua   60
ugcaaaacug augguggccu gc                                          82

<210> SEQ ID NO 97
<211> LENGTH: 22
<212> TYPE: DNA
<213> ORGANISM: Homo sapiens

<400> SEQUENCE: 97
aguuuugcau aguugcacua ca                                          22

<210> SEQ ID NO 98
<211> LENGTH: 71
<212> TYPE: DNA
<213> ORGANISM: Homo sapiens

<400> SEQUENCE: 98
guagcacuaa agugcuuaua gugcaggguag uguuuaguua ucuacugcau uaugagcacu   60
uaaaguacug c                                                      71

<210> SEQ ID NO 99
<211> LENGTH: 23
<212> TYPE: DNA
<213> ORGANISM: Homo sapiens

<400> SEQUENCE: 99
uaaagugcuu auagugcagg uag                                          23

<210> SEQ ID NO 100
<211> LENGTH: 87
<212> TYPE: DNA
<213> ORGANISM: Homo sapiens

<400> SEQUENCE: 100
cacuguucua ugguuaguuu ugcagguuug cauccagcug ugugauauuc ugcugugcaa   60
auccaugcaa aacugacugu gguagug                                     87

<210> SEQ ID NO 101
<211> LENGTH: 23
<212> TYPE: DNA
<213> ORGANISM: Homo sapiens

<400> SEQUENCE: 101
aguuuugcag guuugcaucc agc                                          23

<210> SEQ ID NO 102

```
<211> LENGTH: 78
<212> TYPE: DNA
<213> ORGANISM: Homo sapiens

<400> SEQUENCE: 102
cuuucuacac agguugggau cgguugcaau gcuguguuuc uguaugguau ugcacuuguc    60
ccggccuguu gaguuugg                                                 78

<210> SEQ ID NO 103
<211> LENGTH: 23
<212> TYPE: DNA
<213> ORGANISM: Homo sapiens

<400> SEQUENCE: 103
agguugggau cgguugcaau gcu                                           23

<210> SEQ ID NO 104
<211> LENGTH: 81
<212> TYPE: DNA
<213> ORGANISM: Homo sapiens

<400> SEQUENCE: 104
ccuuggccau guaaaagugc uuacagugca gguagcuuuu ugagaucuac ugcaauguaa    60
gcacuucuua cauuaccaug g                                             81

<210> SEQ ID NO 105
<211> LENGTH: 23
<212> TYPE: DNA
<213> ORGANISM: Homo sapiens

<400> SEQUENCE: 105
aaaagugcuu acagugcagg uag                                           23

<210> SEQ ID NO 106
<211> LENGTH: 71
<212> TYPE: DNA
<213> ORGANISM: Homo sapiens

<400> SEQUENCE: 106
uguguuaagg ugcaucuagu gcaguuagug aagcagcuua gaaucuacug cccuaaaugc    60
cccuucuggc a                                                        71

<210> SEQ ID NO 107
<211> LENGTH: 23
<212> TYPE: DNA
<213> ORGANISM: Homo sapiens

<400> SEQUENCE: 107
uaaggugcau cuagugcagu uag                                           23

<210> SEQ ID NO 108
<211> LENGTH: 69
<212> TYPE: DNA
<213> ORGANISM: Homo sapiens

<400> SEQUENCE: 108
aguaccaaag ugcucauagu gcagguaguu uuggcaugac ucuacuguag uaugggcacu    60
uccaguacu                                                           69

<210> SEQ ID NO 109
<211> LENGTH: 23
```

```
<212> TYPE: DNA
<213> ORGANISM: Homo sapiens

<400> SEQUENCE: 109
caaagugcuc auagugcagg uag                                            23

<210> SEQ ID NO 110
<211> LENGTH: 96
<212> TYPE: DNA
<213> ORGANISM: Homo sapiens

<400> SEQUENCE: 110
acauugcuac uuacaauuag uuuugcaggu uugcauuuca gcguauauau guauaugugg    60
cugugcaaau ccaugcaaaa cugauuguga uaaugu                              96

<210> SEQ ID NO 111
<211> LENGTH: 22
<212> TYPE: DNA
<213> ORGANISM: Homo sapiens

<400> SEQUENCE: 111
aguuuugcag guuugcauuu ca                                             22

<210> SEQ ID NO 112
<211> LENGTH: 75
<212> TYPE: DNA
<213> ORGANISM: Homo sapiens

<400> SEQUENCE: 112
ucaucccugg gugggauuu guugcauuac uuguguucua uauaaaguau ugcacuuguc    60
ccggccugug gaaga                                                     75

<210> SEQ ID NO 113
<211> LENGTH: 22
<212> TYPE: DNA
<213> ORGANISM: Homo sapiens

<400> SEQUENCE: 113
ggguggggau uuguugcauu ac                                             22

<210> SEQ ID NO 114
<211> LENGTH: 75
<212> TYPE: DNA
<213> ORGANISM: Homo sapiens

<400> SEQUENCE: 114
uguugucggg uggaucacga ugcaauuuug augaguauca uaggagaaaa auugcacggu    60
auccaucugu aaacc                                                     75

<210> SEQ ID NO 115
<211> LENGTH: 22
<212> TYPE: DNA
<213> ORGANISM: Homo sapiens

<400> SEQUENCE: 115
cggguggauc acgaugcaau uu                                             22

<210> SEQ ID NO 116
<211> LENGTH: 50
<212> TYPE: DNA
<213> ORGANISM: Homo sapiens
```

```
<400> SEQUENCE: 116
tctaacactc ttcctcctac aaactatatt tatatccaac tataaatacc            50

<210> SEQ ID NO 117
<211> LENGTH: 50
<212> TYPE: DNA
<213> ORGANISM: Homo sapiens

<400> SEQUENCE: 117
tcaactactc aaaaaccaca ataatccct aacaacttcc ctaacaaaca             50

<210> SEQ ID NO 118
<211> LENGTH: 50
<212> TYPE: DNA
<213> ORGANISM: Homo sapiens

<400> SEQUENCE: 118
cttaatttta aatcctcaac ttctaaaaca acrcaaaaca cacaataaac            50

<210> SEQ ID NO 119
<211> LENGTH: 50
<212> TYPE: DNA
<213> ORGANISM: Homo sapiens

<400> SEQUENCE: 119
tattactctt ccaaaataca cacaaaaaac aataaaaccc aaaaaattac            50

<210> SEQ ID NO 120
<211> LENGTH: 50
<212> TYPE: DNA
<213> ORGANISM: Homo sapiens

<400> SEQUENCE: 120
ctaccttaat tcaaatttat caaaaacaaa atctaaaata aaacttcaac            50

<210> SEQ ID NO 121
<211> LENGTH: 50
<212> TYPE: DNA
<213> ORGANISM: Homo sapiens

<400> SEQUENCE: 121
ttcctcttaa aacacttata tatttaaaat caaaataatc ttcccatctc            50

<210> SEQ ID NO 122
<211> LENGTH: 50
<212> TYPE: DNA
<213> ORGANISM: Homo sapiens

<400> SEQUENCE: 122
aataaatcaa taacacaata ccacctacaa aaacatcaaa accacaacca            50

<210> SEQ ID NO 123
<211> LENGTH: 50
<212> TYPE: DNA
<213> ORGANISM: Homo sapiens

<400> SEQUENCE: 123
tctaacaccc taaaaaaacc taaaacttca aaaataaaaa caaaaccaac            50

<210> SEQ ID NO 124
<211> LENGTH: 50
<212> TYPE: DNA
<213> ORGANISM: Homo sapiens
```

```
<400> SEQUENCE: 124
aataaaaaaa atcacaacaa ctacaacaac cataacaact acaaaaacca          50

<210> SEQ ID NO 125
<211> LENGTH: 50
<212> TYPE: DNA
<213> ORGANISM: Homo sapiens

<400> SEQUENCE: 125
ccaataccaa aaaatatcaa ataatattca tcaaaaaaac taaaccaacc          50

<210> SEQ ID NO 126
<211> LENGTH: 50
<212> TYPE: DNA
<213> ORGANISM: Homo sapiens

<400> SEQUENCE: 126
ataaaaaaat taaaccaact aacraccccct acaaactcaa aataaaaaac         50

<210> SEQ ID NO 127
<211> LENGTH: 50
<212> TYPE: DNA
<213> ORGANISM: Homo sapiens

<400> SEQUENCE: 127
ttatctccaa ctaaaaaaac acaaacaac caaaaaacta aaaacaaca            50

<210> SEQ ID NO 128
<211> LENGTH: 50
<212> TYPE: DNA
<213> ORGANISM: Homo sapiens

<400> SEQUENCE: 128
aaaactacca caaaatcata acttctttt ttttcttaaa ataaaatctc           50

<210> SEQ ID NO 129
<211> LENGTH: 50
<212> TYPE: DNA
<213> ORGANISM: Homo sapiens

<400> SEQUENCE: 129
ataaaatcac ccaaccacac tcaaataaaa cccaaaaata aacaaaaaca          50

<210> SEQ ID NO 130
<211> LENGTH: 50
<212> TYPE: DNA
<213> ORGANISM: Homo sapiens

<400> SEQUENCE: 130
atctcataat tcaccatttt ttaaacccat caaaaaaaca caatattcca          50

<210> SEQ ID NO 131
<211> LENGTH: 50
<212> TYPE: DNA
<213> ORGANISM: Homo sapiens

<400> SEQUENCE: 131
ttttataaac ttaaacaaat aatataacta atctaaacct caatttcctc          50

<210> SEQ ID NO 132
<211> LENGTH: 50
<212> TYPE: DNA
```

<213> ORGANISM: Homo sapiens

<400> SEQUENCE: 132
acaaactcct aactactaaa actaaacaaa acactaaaaa aataaaacca          50

<210> SEQ ID NO 133
<211> LENGTH: 50
<212> TYPE: DNA
<213> ORGANISM: Homo sapiens

<400> SEQUENCE: 133
acaaacacaa ataaacaaaa ctacacaaaa acctataaac aaacaaaaca          50

<210> SEQ ID NO 134
<211> LENGTH: 50
<212> TYPE: DNA
<213> ORGANISM: Homo sapiens

<400> SEQUENCE: 134
acctcataaa catctaaact ataacrctta aaattcctaa ataatctctc          50

<210> SEQ ID NO 135
<211> LENGTH: 50
<212> TYPE: DNA
<213> ORGANISM: Homo sapiens

<400> SEQUENCE: 135
aacaaaaata aaactatatc aacttcccac aaatactcaa aacactaaac          50

<210> SEQ ID NO 136
<211> LENGTH: 50
<212> TYPE: DNA
<213> ORGANISM: Homo sapiens

<400> SEQUENCE: 136
ttattacaat tctcattaaa aaatttctct ttaaacataa acttaataac          50

<210> SEQ ID NO 137
<211> LENGTH: 50
<212> TYPE: DNA
<213> ORGANISM: Homo sapiens

<400> SEQUENCE: 137
aaaaataaaa ccaccccat attttcccra aacraaactt acaataaacc           50

<210> SEQ ID NO 138
<211> LENGTH: 50
<212> TYPE: DNA
<213> ORGANISM: Homo sapiens

<400> SEQUENCE: 138
aaaaacccaa ctaataaaaa cccaactaat aaaaaccaa aaaacaaca            50

<210> SEQ ID NO 139
<211> LENGTH: 50
<212> TYPE: DNA
<213> ORGANISM: Homo sapiens

<400> SEQUENCE: 139
aaaacaaaac ttaacaaaaa taaaatctta aaaaatcaca aatcacaaca          50

<210> SEQ ID NO 140
<211> LENGTH: 50

<212> TYPE: DNA
<213> ORGANISM: Homo sapiens

<400> SEQUENCE: 140
tctcrcaatt accaaaatac aaaatactca atcccatat ataaaataac         50

<210> SEQ ID NO 141
<211> LENGTH: 50
<212> TYPE: DNA
<213> ORGANISM: Homo sapiens

<400> SEQUENCE: 141
tcacaaaaat aacaaaaata aaactcaaac atatcaaact acaaatccca         50

<210> SEQ ID NO 142
<211> LENGTH: 50
<212> TYPE: DNA
<213> ORGANISM: Homo sapiens

<400> SEQUENCE: 142 aatatcccctt ttattatcaa tcaaaataaa ctaatttata ctacaataac        50

<210> SEQ ID NO 143
<211> LENGTH: 50
<212> TYPE: DNA
<213> ORGANISM: Homo sapiens

<400> SEQUENCE: 143
ttaataatat aattaatcac aaaaaatcac cataaatcaa accaaataca         50

<210> SEQ ID NO 144
<211> LENGTH: 50
<212> TYPE: DNA
<213> ORGANISM: Homo sapiens

<400> SEQUENCE: 144
taacccatta tcaacrtcat taaaatccaa atttcractc acaaaaaacc         50

<210> SEQ ID NO 145
<211> LENGTH: 50
<212> TYPE: DNA
<213> ORGANISM: Homo sapiens

<400> SEQUENCE: 145
aaattacata ataactcaaa aacaaacaaa atatccaaaa aaaactaacc         50

<210> SEQ ID NO 146
<211> LENGTH: 50
<212> TYPE: DNA
<213> ORGANISM: Homo sapiens

<400> SEQUENCE: 146
ttcctataat aattaaaaaa acataccaaa ttttccttt accctttac          50

<210> SEQ ID NO 147
<211> LENGTH: 50
<212> TYPE: DNA
<213> ORGANISM: Homo sapiens

<400> SEQUENCE: 147
ataaccacaa aaatcacaaa acaaacataa acaaaaataa aaatacaaca         50

<210> SEQ ID NO 148

```
<211> LENGTH: 50
<212> TYPE: DNA
<213> ORGANISM: Homo sapiens

<400> SEQUENCE: 148
ttccacctac accaataatt tataaaacaa ccaaaaattt ataaaaaaac        50

<210> SEQ ID NO 149
<211> LENGTH: 50
<212> TYPE: DNA
<213> ORGANISM: Homo sapiens

<400> SEQUENCE: 149
ctcaaatcaa tccacaaaaa ataaccccct accaataaaa aacaacccca        50

<210> SEQ ID NO 150
<211> LENGTH: 50
<212> TYPE: DNA
<213> ORGANISM: Homo sapiens

<400> SEQUENCE: 150
aacacaaaaa ctacaaaaac acaaaaaaac atataccccct taaattccca       50

<210> SEQ ID NO 151
<211> LENGTH: 50
<212> TYPE: DNA
<213> ORGANISM: Homo sapiens

<400> SEQUENCE: 151 ctcccccccac cactatctcc aaataaaaaa atcaaaaata acaaaaacca       50

<210> SEQ ID NO 152
<211> LENGTH: 50
<212> TYPE: DNA
<213> ORGANISM: Homo sapiens

<400> SEQUENCE: 152
accaaaaatc caccccaaaa cctctacaac cctaaaaaaa caaaataaca        50

<210> SEQ ID NO 153
<211> LENGTH: 50
<212> TYPE: DNA
<213> ORGANISM: Homo sapiens

<400> SEQUENCE: 153
atattacttc tacaccaata taaaattaaa aaattctaaa acaaaccatc        50

<210> SEQ ID NO 154
<211> LENGTH: 50
<212> TYPE: DNA
<213> ORGANISM: Homo sapiens

<400> SEQUENCE: 154
aaaacaaaac aacaacataa accaaaacaa aaatacaaaa aaacaacaca        50

<210> SEQ ID NO 155
<211> LENGTH: 50
<212> TYPE: DNA
<213> ORGANISM: Homo sapiens

<400> SEQUENCE: 155
ctcttaaaac atcaccccac ctaaaaaaaa tttaaaacat aaaataaacc        50
```

```
<210> SEQ ID NO 156
<211> LENGTH: 50
<212> TYPE: DNA
<213> ORGANISM: Homo sapiens

<400> SEQUENCE: 156
tcaataaacc cttccttcaa acaaacccca aaatcaccac aaaataatca            50

<210> SEQ ID NO 157
<211> LENGTH: 50
<212> TYPE: DNA
<213> ORGANISM: Homo sapiens

<400> SEQUENCE: 157
taaactaaat atatccctaa aaaacataaa aaaacccaaa tacaaaaacc            50

<210> SEQ ID NO 158
<211> LENGTH: 50
<212> TYPE: DNA
<213> ORGANISM: Homo sapiens

<400> SEQUENCE: 158
tataacacta aacctaacat aatatcctat acctataacc ctaactactc            50

<210> SEQ ID NO 159
<211> LENGTH: 50
<212> TYPE: DNA
<213> ORGANISM: Homo sapiens

<400> SEQUENCE: 159
aacaaaaaac tcaaataaca acaccaaaaa ctcaacacaa caaaacaaca            50

<210> SEQ ID NO 160
<211> LENGTH: 50
<212> TYPE: DNA
<213> ORGANISM: Homo sapiens

<400> SEQUENCE: 160
ccacaaaaat caataaaata tttctaaatt tctttatttc aataaacttc            50

<210> SEQ ID NO 161
<211> LENGTH: 50
<212> TYPE: DNA
<213> ORGANISM: Homo sapiens

<400> SEQUENCE: 161
aaaaatttca caaaattttt tctcaaaaat ataccacaat acaaactaac            50

<210> SEQ ID NO 162
<211> LENGTH: 50
<212> TYPE: DNA
<213> ORGANISM: Homo sapiens

<400> SEQUENCE: 162
aaaaaaataa ctcaccttaa aaaataccaa actaaaacta aatcctttcc            50

<210> SEQ ID NO 163
<211> LENGTH: 50
<212> TYPE: DNA
<213> ORGANISM: Homo sapiens

<400> SEQUENCE: 163
aataaatcat aaatctattt cctaaaacaa ttatctacaa ccataccacc            50
```

<210> SEQ ID NO 164
<211> LENGTH: 50
<212> TYPE: DNA
<213> ORGANISM: Homo sapiens

<400> SEQUENCE: 164
aaccacaaaa cttttacaa acccataaaa aaacaacct aaaaaacttc         50

<210> SEQ ID NO 165
<211> LENGTH: 50
<212> TYPE: DNA
<213> ORGANISM: Homo sapiens

<400> SEQUENCE: 165
aacaactaaa aaacttacat ctaaaatccc tcaaaaaact ttttattaac         50

<210> SEQ ID NO 166
<211> LENGTH: 50
<212> TYPE: DNA
<213> ORGANISM: Homo sapiens

<400> SEQUENCE: 166
acctaaaacc cccaacaaaa ataaaaaacc aaaataaatc ctaacatcca         50

<210> SEQ ID NO 167
<211> LENGTH: 50
<212> TYPE: DNA
<213> ORGANISM: Homo sapiens

<400> SEQUENCE: 167
taaatccrta ctactctaac tttaaacata ccttctaaat acaacaaccc         50

<210> SEQ ID NO 168
<211> LENGTH: 50
<212> TYPE: DNA
<213> ORGANISM: Homo sapiens

<400> SEQUENCE: 168
crcratccrt attaaaaaaa actccraaaa taatacactc ctaaaaaaac         50

<210> SEQ ID NO 169
<211> LENGTH: 50
<212> TYPE: DNA
<213> ORGANISM: Homo sapiens

<400> SEQUENCE: 169
attaccttct ttctttcttt ctattttttt aaataaaacc ttactctatc         50

<210> SEQ ID NO 170
<211> LENGTH: 50
<212> TYPE: DNA
<213> ORGANISM: Homo sapiens

<400> SEQUENCE: 170
tcaactactc aaaaaccgca aataatccct aacaacttcc ctaacgaacg         50

<210> SEQ ID NO 171
<211> LENGTH: 50
<212> TYPE: DNA
<213> ORGANISM: Homo sapiens

<400> SEQUENCE: 171
aataaatcaa taacacaata ccgcctacaa aaacatcaaa accgcgaccg         50

<210> SEQ ID NO 172
<211> LENGTH: 50
<212> TYPE: DNA
<213> ORGANISM: Homo sapiens

<400> SEQUENCE: 172
aataaaaaaa atcgcaacaa ctacaacaac cgtaacgact acgaaaaccg        50

<210> SEQ ID NO 173
<211> LENGTH: 50
<212> TYPE: DNA
<213> ORGANISM: Homo sapiens

<400> SEQUENCE: 173
ttatctccaa ctaaaaaaac gcgaaacgac caaaaaacta aaaaacaacg        50

<210> SEQ ID NO 174
<211> LENGTH: 50
<212> TYPE: DNA
<213> ORGANISM: Homo sapiens

<400> SEQUENCE: 174
ataaaatcac ccgaccacac tcgaataaaa cccaaaaata aacgaaaacg        50

<210> SEQ ID NO 175
<211> LENGTH: 50
<212> TYPE: DNA
<213> ORGANISM: Homo sapiens

<400> SEQUENCE: 175
atctcataat tcaccgttttt ttaaacccgt cgaaaaaacg caatattccg        50

<210> SEQ ID NO 176
<211> LENGTH: 50
<212> TYPE: DNA
<213> ORGANISM: Homo sapiens

<400> SEQUENCE: 176
acgaactcct aactactaaa actaaacgaa acgctaaaaa aataaaaccg        50

<210> SEQ ID NO 177
<211> LENGTH: 50
<212> TYPE: DNA
<213> ORGANISM: Homo sapiens

<400> SEQUENCE: 177
acgaacacaa ataaacgaaa ctacgcgaaa acctataaac gaacgaaacg        50

<210> SEQ ID NO 178
<211> LENGTH: 50
<212> TYPE: DNA
<213> ORGANISM: Homo sapiens

<400> SEQUENCE: 178
aaaaacccga ctaataaaaa cccgactaat aaaaaaccga aaaaacaacg        50

<210> SEQ ID NO 179
<211> LENGTH: 50
<212> TYPE: DNA
<213> ORGANISM: Homo sapiens

<400> SEQUENCE: 179
aaaacgaaac ttaacgaaaa taaaatctta aaaaatcgca aatcgcgacg    50

<210> SEQ ID NO 180
<211> LENGTH: 50
<212> TYPE: DNA
<213> ORGANISM: Homo sapiens

<400> SEQUENCE: 180
tcacgaaaat aacaaaaata aaactcgaac atatcaaact acaaatcccg    50

<210> SEQ ID NO 181
<211> LENGTH: 50
<212> TYPE: DNA
<213> ORGANISM: Homo sapiens

<400> SEQUENCE: 181
ttaataatat aattaatcac aaaaaatcgc cgtaaatcaa accgaatacg    50

<210> SEQ ID NO 182
<211> LENGTH: 50
<212> TYPE: DNA
<213> ORGANISM: Homo sapiens

<400> SEQUENCE: 182
ataaccacga aaatcacaaa acaaacataa acaaaaataa aaatacgacg    50

<210> SEQ ID NO 183
<211> LENGTH: 50
<212> TYPE: DNA
<213> ORGANISM: Homo sapiens

<400> SEQUENCE: 183
ctcaaatcga tccacgaaaa aataaccoct accaataaaa aacaaccccg    50

<210> SEQ ID NO 184
<211> LENGTH: 50
<212> TYPE: DNA
<213> ORGANISM: Homo sapiens

<400> SEQUENCE: 184
aacgcgaaaa ctacaaaaac acgaaaaaac gtataccoct taaattcccg    50

<210> SEQ ID NO 185
<211> LENGTH: 50
<212> TYPE: DNA
<213> ORGANISM: Homo sapiens

<400> SEQUENCE: 185 ctcccccac cactatctcc aaataaaaaa atcgaaaata acaaaaaccg    50

<210> SEQ ID NO 186
<211> LENGTH: 50
<212> TYPE: DNA
<213> ORGANISM: Homo sapiens

<400> SEQUENCE: 186
accaaaaatc caccccaaaa cctctacgac cctaaaaaaa caaaataacg    50

<210> SEQ ID NO 187
<211> LENGTH: 50
<212> TYPE: DNA
<213> ORGANISM: Homo sapiens

<400> SEQUENCE: 187

```
aaaacgaaac aacaacgtaa accaaaacaa aaatacaaaa aaacaacgcg        50

<210> SEQ ID NO 188
<211> LENGTH: 50
<212> TYPE: DNA
<213> ORGANISM: Homo sapiens

<400> SEQUENCE: 188
tcaataaacc cttccttcga acgaacccca aaatcaccgc aaaataatcg        50

<210> SEQ ID NO 189
<211> LENGTH: 50
<212> TYPE: DNA
<213> ORGANISM: Homo sapiens

<400> SEQUENCE: 189
aacgaaaaac tcaaataaca acgccaaaaa ctcaacacga cgaaacgacg        50

<210> SEQ ID NO 190
<211> LENGTH: 50
<212> TYPE: DNA
<213> ORGANISM: Homo sapiens

<400> SEQUENCE: 190
acctaaaacc cccaacgaaa ataaaaaacc gaaataaatc ctaacgtccg        50

<210> SEQ ID NO 191
<211> LENGTH: 21
<212> TYPE: DNA
<213> ORGANISM: Homo sapiens

<400> SEQUENCE: 191
ucacagugaa ccggucucuu u                                       21
```